United States Patent [19]
Folkman et al.

[11] Patent Number: 5,175,147
[45] Date of Patent: Dec. 29, 1992

[54] ACID-RESISTANT FGF COMPOSITION AND METHOD OF TREATING ULCERATING DISEASES OF THE GASTROINTESTINAL TRACT

[75] Inventors: Moses J. Folkman, Brookline, Mass.; Koichi Kato, Kawabe, Japan

[73] Assignees: Takeda Chemical Industries, Ltd, Japan; Children's Medical Center Corporation

[21] Appl. No.: 382,263

[22] Filed: Jul. 20, 1989

Related U.S. Application Data

[63] Continuation-in-part of Ser. No. 234,966, Aug. 19, 1988, abandoned.

[51] Int. Cl.⁵ .................. A61K 37/36; A61K 37/02
[52] U.S. Cl. .................................. 514/12; 514/21; 514/925; 514/926; 514/927; 514/928; 514/970; 514/778; 514/777
[58] Field of Search ................ 514/12, 21, 925-928, 514/970, 777-8

[56] References Cited

U.S. PATENT DOCUMENTS

| | | | |
|---|---|---|---|
| 4,604,234 | 8/1986 | Fujii | 514/6 |
| 4,689,229 | 8/1987 | Banik | 514/925 |
| 4,745,098 | 5/1988 | Michaeli | 514/54 |
| 4,816,561 | 3/1989 | Todaro | 530/326 |

FOREIGN PATENT DOCUMENTS

| | | |
|---|---|---|
| 237966 | 3/1987 | European Pat. Off. |
| 275204 | 1/1988 | European Pat. Off. |
| 298723 | 7/1988 | European Pat. Off. |
| 320148 | 6/1989 | European Pat. Off. |
| 8401106 | 3/1984 | PCT Int'l Appl. |
| 8701728 | 3/1987 | PCT Int'l Appl. |

OTHER PUBLICATIONS

Seno, Biochemical and Biophysical Research Communications, 151, No. 2, 701-708, 15 Mar. 1988.
P. A. Walicke, et al., Experimental Neurology, vol. 102, pp. 144-148 (1988).
K. A. Thomas, FASEB Journal, vol. 1, pp. 434-440 (1987).
R. R. Lobb, et al., Biochemistry, vol. 24, pp. 4969-4973 (1985).
Gospodarowicz et al., Endocrine Reviews, vol. 8, pp. 95-114 (1987).
Newswatch, Oct. 5, 1987, page 5.
G. M. Fox et al., The Journal of Biological Chemistry, vol. 263, pp. 18452-18458 (1988).
K. J. Anderson et al., Nature vol. 332, pp. 360-361 (1988).
R. S. Morrison et al., Proc. Natl. Acad. Sci. USA vol. 83, pp. 7537-7541 (1986).

Primary Examiner—F. T. Moezie
Attorney, Agent, or Firm—David G. Conlin; Gregory D. Williams; David S. Resnick

[57] ABSTRACT

This invention describes pharmaceutical compositions and methods of treating ulcerating diseases of the gastrointestinal tract in mammals with an acid-resistant fibroblast growth factor compositions. Also described is the use of acid-resistant fibroblast growth factor compositions in the treatment of various other fibroblast growth factor-responsive conditions.

18 Claims, 12 Drawing Sheets

```
                  BspMI
     10       ↓   20         30          40          50          60
AAGCTTACCT GCCATGTTTA ATCTGCCTCC CGGGAATTAC AAGAAGCCCA AACTCCTCTA 70          80         90         100         110         120
CTGCAGCAAC GGGGCCACT TCCTGAGGAT TCTTCCGGAT GGCACAGTGG ATGGACAAG 130         140        150         160         170         180
GGACAGGAGC GACCAGCACA TTCAGCTGCA ACTCAGTGCG GAAAGCGTGG GGGAGGTGTA 190         200        210         220         230         240
TATAAAGAGT ACCGAGACTG GCCAGTACTT GGCAATGGAC ACCGACGGGC TTTTATACGG 250         260        270         280         290         300
CTCACAGACA CCAAATGAGG AATGTTTGTT CCTGGAAAGG CTGGAGGAGA ACCATTACAA 310         320        330         340         350         360
CACCTATATA TCCAAGAAGC ATGCAGAGAA GAATTGGTTT GTTGGCCTCA AGAAGAATGG 370         380        390         400         410         420
GAGCTGCAAA CGCGGTCCTC GGACTCACTA TGGCCAGAAA GCAATCTTGT TTCTCCCCCT 430         440        450         460         470         480
GCCAGTCTCT TCTGATTAAT AAGGATCCGA ATTC
                                ↑
                              BamHI
```

FIG. 1

(1) 5'-CGTTCTTGCTGTAGAGCCGCT-3'
                    SER
(RsaI)

(2) 5'-AACGATTAGCGCTCACTCC-3'
            SER
HaeII (3) 5'-GTAACAGACTTAGAAGCTAGT-3'
           SER
AluI (4) 5'-TCGAAGAAGAAAGACTCATCC-3'
           SER
HinfI

FIG. 6

```
MetProAlaLeuProGluAspGlyGlySerGlyAlaPheProProGlyHisPheLysAsp                      20
ATGCCAGCATTGCCCGAGGATGGCGGCAGCGGCGGCCTTCCCGCCCGGCCACTTCAAGGAC                     60

ProLysArgLeuTyrSerLysAsnGlyLeuGlyPheLeuArgIleHisProAspGlyArg                       40
CCCAAGCGGCTCTACAGCAAGAACGGGGGGCTTCTTCCTGCGCATCCACCCCGACGGCCGA                    120

ValAspGlyValArgGluLeuLysSerAspProHisIleLeuLysLeuGlnLeuAlaGluGlu                    60
GTTGACGGGGTCCGGGAGAGAGCGACCCTCACATCCTCAAGCTACAACTTCAAGCAGAAGAG                   180

ArgGlyValValSerIleLeuLysGlyValCysAlaAsnArgTyrLeuAlaMetLysGluAsp                    80
AGAGGAGTTGTGTCTATCAAAGGAGTGTGTGCTAACCGTTACCTGGCTATGAAGGAAGAT                     240

GlyArgLeuLeuAlaSerLysCysValThrAspGluCysPhePheGluArgLeuGluGlu                      100
GGAAGATTACTGGCTTCTAAATGTGTTACGGATGAGTGTTTCTTTTTGAACGATTGGAA                      300

SerAsnAsnTyrArgAsnThrTyrArgSerArgLysTyrThrThrSerTrpTyrValAlaLeuLys                120
TCTAATAACTACACAATACTACCGGTCAAGGAAATACACCACCAGTTGGTATGTGGCACTGAAA                 360

ArgThrGlyGlnTyrLysLeuGlySerLysThrGlyProGlyGlnLysAlaIleLeuPhe                      140
CGAACTGGGCAGTATAAACTTGGATCCAAAACAGGACCTGGGCAGAAAGCTATACTTTTT                     420

LeuProMetSerAlaLysSerTrM                                                          147
CTTCCAATGTCTGCTAAGAGCTGA                                                          444
```

FIG. 7

```
MetProAlaLeuProGluAspGlyLeuGlySerGlyAlaPheProProGlyHisPheLysAsp                    20
ATGCCAGCATTGCCCGAGGATGGCGGAAGCGGGGCCTTCCCGCCGGGCCACTTCAAGGAC                       60

ProLysArgLeuTyrCysLysLysAsnGlyLeuGlyPhePheLeuArgIleHisProAspGlyArg                 40
CCCAAGCGGCTGTACTGCAAAAACGGGGGCTTCTTCCTGCGCATCCACCCCGACGGCCGA                      120

ValAspGlyValArgGluLysSerAspProHisIleLysLeuGlnLeuGlnAlaGluGlu                       60
GTTGACGGGGTCCGGGAGAAGAGCGACCCTCACATCAAGCTACAACTTCAAGCAGAAGAG                      180

ArgGlyValValSerIleLeuLysGlyValSerAlaAsnArgTyrLeuAlaMetLysGluAsp                    80
AGAGGAGTTGTGTCTATCAAGGAGTGAGCTAATCGTTACCTGGCTATGAAGGAAGAT                         240

GlyArgLeuLeuAlaSerLysSerValThrAspGluCysPhePheGluArgLeuGlu                         100
GGAAGATTACTAGCTTCTAAGTCTGTTACGGATGAGTGTTCTTTTTGAACGATTGGAA                        300

SerAsnAsnTyrAsnThrTyrArgSerArgLysTyrThrSerTrpTyrValAlaLeuLys                      120
TCTAATAACTACAATACTTACCGGTCAAGGAAATACACCAGTTGGTATGTGGCACTGAAA                      360

ArgThrGlyLeuGlnTyrLysLeuGluGlySerLysThrGlyProGlyLysGlnLysAlaIleLeuPhe             140
CGAACTGGGCAGTATAAACTTGGATCCAAAAACAGGACCTGGGCAGAAAGTATACTTTTT                      420

LeuProMetSerAlaLysSerTrm                                                         147
CTTCCAATGTCTGCTAAGAGCTGA                                                         444
```

FIG. 9

ACID-RESISTANT FGF COMPOSITION AND METHOD OF TREATING ULCERATING DISEASES OF THE GASTROINTESTINAL TRACT

The present application is a continuation-in-part of U.S. Ser. No. 07/234,966 filed Aug. 19, 1988 (now abandoned).

The present invention relates to acid-resistant fibroblast growth factor compositions, and to methods of treating ulcerating diseases of the gastrointestinal tract in mammals with acid-resistant fibroblast growth factor compositions. This invention also relates to the use of acid-resistant fibroblast growth factor compositions in the treatment of various other fibroblast growth factor-responsive conditions especially where acid and/or heat labile fibroblast growth factor has comparatively less therapeutic value.

BACKGROUND OF THE INVENTION

Ulcerating diseases of the gastrointestinal tract, commonly referred to as peptic ulcers, are diseases in which there is a defect in the epithelium of the gastrointestinal tract. This type of defect usually occurs through the combined action of hydrochloric acid and pepsin. By definition, peptic ulcers penetrate to at least the submucosa; more superficial lesions are referred to as erosions. Peptic ulcers may occur in many locations of the gastrointestinal tract including the stomach, duodenum or esophagus, in Meckel's diverticulum, at the sight of a surgically created anastomosis, and, rarely, in the upper jejunum.

Twenty years ago, treatment of peptic ulceration consisted of bedrest, a bland diet, antacids, and/or surgical removal of the affected area. More recently, $H_2$-receptor antagonists have been used in the treatment of peptic ulcers. The two most commonly used $H_2$-receptor antagonists are ranitidine and cimetidine, both of which act therapeutically by inhibiting gastric acid secretion. The effectiveness and unwanted effects of these two antagonists has been extensively studied, e.g., by Thomas et al., in *Clinics in Gastroenterology*, Volume 13, Number 2, at pages 501-529.

While treatment with these antagonists has been widespread and relatively successful, many peptic ulcers do not respond to $H_2$-receptor antagonist therapy. For example, while the reasons are not clearly understood, some 20 to 30% of duodenal ulcers do not heal after four to six weeks of therapy with either oimetidine or ranitidine. Moreover, recurrence or relapse of the ulcerating condition is not uncommon with $H_2$-receptor antagonists.

Fibroblast growth factor (FGF), has been shown to be a potent angiogenic factor which, inter alia, is responsible for neovascularization in wound healing. There are two types of FGF, acidic fibroblast growth factor (aFGF) and basic fibroblast growth factor (bFGF). aFGF and bFGF are, however, acid and/or heat labile. Thus, prior to the present invention, the use of FGF in acid and/or heat environments such as in the treatment of peptic ulcers has not been possible.

SUMMARY OF THE INVENTION

In accordance with the present invention, there is provided a novel method of treating mammals having a disease which is FGF-responsive, which comprises administering to the mammal an effective amount of an acid-resistant FGF composition or a pharmaceutically acceptable salt thereof. Specifically, the present invention provides a method of treating mammals having an ulcerating disease of the gastrointestinal tract which comprises administering an effective amount of an acid-resistant FGF composition to the mammal. More specifically, the present invention provides a method for treating peptic ulcers and other diseases, especially those which would otherwise be responsive to FGF treatment but for existence of an acid environment.

Preferably, the acid-resistant FGF composition of the present invention is administered in a pharmaceutically acceptable vehicle in conjunction or in combination with one or more of the following: (a) stabilizing agents; (b) antisecretory agents such as $H_2$-receptor antagonists; (c) cytoprotective agents; and (d) antacids.

Acid-resistant FGF compositions in accordance with the present invention, when administered to mammals with ulcerating diseases of the gastrointestinal tract, result in virtually complete healing of the ulcer. When compared with the above-described $H_2$-receptor antagonists, the best result for the antagonists was less than or equal to result achieved with approximately 10% of the optimal amount of the acid-resistant FGF composition.

BRIEF DESCRIPTION OF THE DRAWINGS

FIG. 1 shows the base sequence of the cDNA which codes for the human acidic FGF in Example 4.

FIG. 6 shows the synthetic oligomers used as primers to mutate Cys-encoding codons to Ser-encoding codons FIG. 7 shows the base sequence which encodes the human bFGF mutein CS1, carried by the plasmid pTB739 obtained in Example 9.2, and the amino acid sequence of the human bFGF mutein CS1, encoded thereby. The mutated bases are underlined, and the region containing the converted amino acid is surrounded by the square.

FIG. 9 shows the base sequence which encodes the human bFGF mutein CS23, carried by the plasmid pTB762 obtained in Example 9.4, and the amino acid sequence of the human bFGF mutein CS23, encoded thereby. The mutated bases are underlined, and the regions containing either of the converted amino acids are surrounded by the squares.

DETAILED DESCRIPTION OF THE INVENTION

Figure 2:
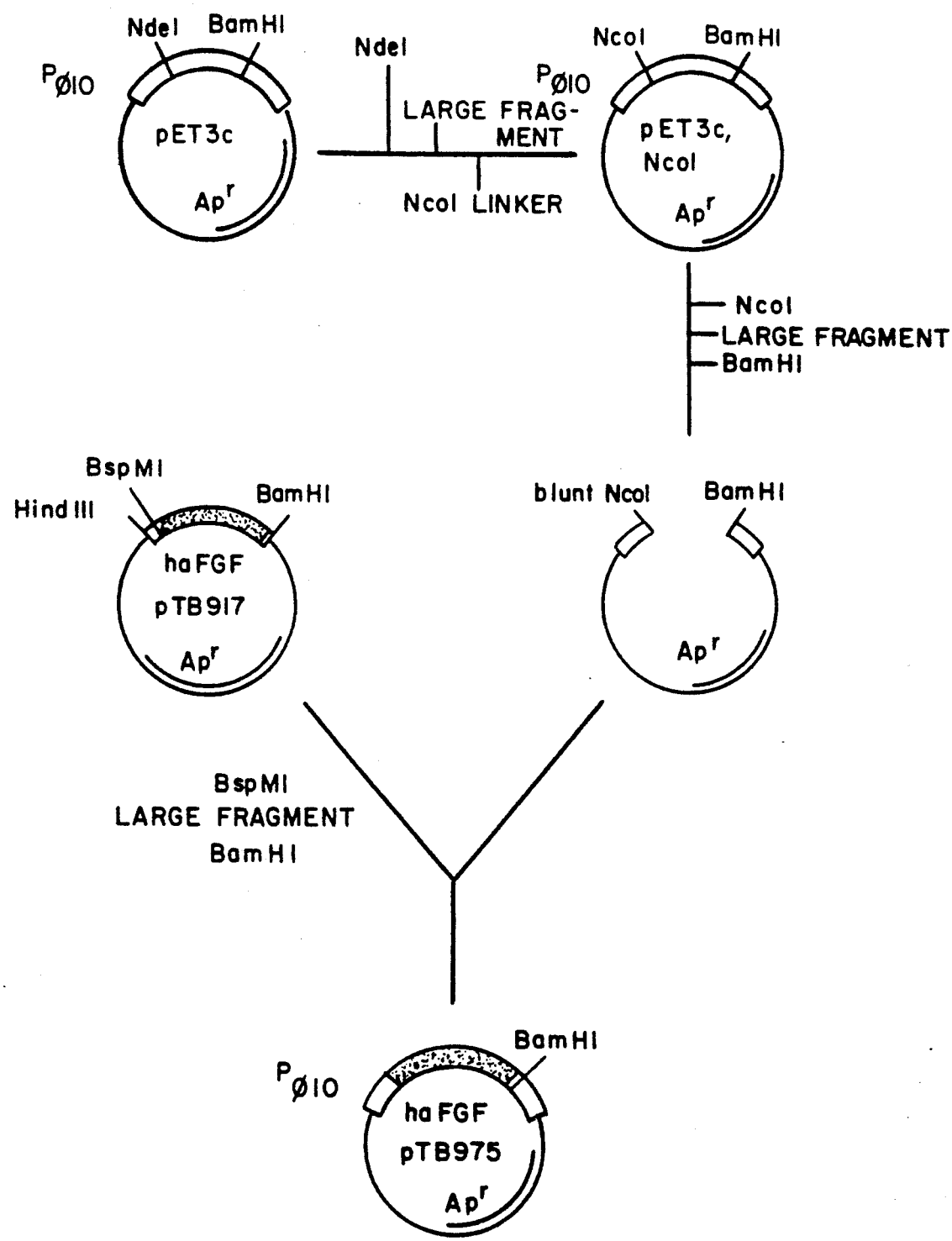
FIG. 2 shows the construction scheme of the plasmid TB975 in Example 4.

The present invention provides novel compositions and methods for the treatment and/or prevention of FGF-responsive diseases in mammals. The method, in its simplest form, comprises administering to the mammal an effective amount of an acid-resistant FGF composition or a pharmaceutically acceptable salt thereof. The invention also provides for certain pharmaceutical compositions comprising acid-resistant FGF or its salt, and one or more agents which stabilize, potentiate, or otherwise affect the therapeutic efficacy of acid-resistant FGF. Such agents include: (i) stabilizing agents such as glycosaminoglycan which include heparin, glucan sulfate such as dextran sulfate, sulfated cyclodextrins such as beta-cyclodextrin tetradecasulfate and β-1,3-glucan sulfate; (ii) antisecretory agents such as H₂-receptor antagonists (e.g., cimetidine, ranitidine, famotidine, roxatidine acetate), muscarine receptor antagonists (e.g., pirenzepine); (iii) cytoprotective agents such as spizofurone and prostaglandin derivatives, and; (iv) antacids such as aluminum hydroxide gel, sodium bicarbonate and sucralfate. Such agents may be administered either separately or as a component of the composition.

In accordance with the present invention, various ulcerating diseases of the gastrointestinal tract may be treated by administering to the mammal an effective amount of the acid-resistant FGF composition. Such ulcerating diseases include regional ileitis, ulcerated colitis and peptic ulcer (either duodenal or gastric).

The acid-resistant FGF composition of the present invention can also be used to treat other conditions in mammals which would be responsive to FGF therapy but for the existence of an acidic environment. For example, in cancer treatment of bladders, there often results ulcerations of that organ's tissue which could be treated with FGF if the FGF were acid-resistant. Bandaged wounds can also produce an acid environment which would respond to acid-resistant FGF. Other conditions in which there is an acid environment and which would otherwise be responsive to FGF therapy will be apparent to the skilled artisan.

The acid-resistant FGF composition of the present invention may be a composition of either aFGF or bFGF. aFGF and bFGF useful in practicing the present invention may be derived from a number of sources including mammals such as human, bovine, monkey, swine and equine.

Acid-resistant FGF compositions useful in practicing the present invention include: (i) acid-resistant native mammalian FGF such as aFGF (ii) native mammalian FGF which is stabilized by stabilizing agents; (iii) FGF which is modified to be acid-resistant; or (iv) modified FGF which is further stabilized by stabilizing agents.

The preferred acid-resistant FGF composition is one which includes a modified FGF such as a purified recombinant human basic FGF (rhbFGF) protein in which a mutation is induced ("mutein") by changing one or more of the four cysteines present at amino acid residues 25, 69, 87, and 92 of the mature protein to serine. In numbering the human bFGF-constitueny amino acids, the N-terminal Pro is comprises the first amino acid. The most preferred acid-resistant FGF is the rhbFGF mutein CS23, the structure of which is more fully described in Senoo et al., Biochemical and Biophysical Research Communications, Vol. 151, No. 2, 701–708 (1988) and in U.S. Ser. No. 161,123, filed Feb. 18, 1988, which corresponds to EP-281,822 A2, the disclosures of which are hereby incorporated by reference herein. Other muteins which can be used in practicing the present invention and which are also described in these references include muteins in which amino acid(s) have been added, and where constituent amino acid(s) have been deleted or substituted.

While not to be bound by theory, it is believed that the substitution of neutral amino acids such as serine or alanine for cysteine residues in FGF stabilizes the FGF to heat, acid and certain enzymes which degrade FGF. This type of substitution is believed to cause minimal alteration to the structure and activity of the protein because the substitution of an oxygen atom (serine) for a sulfur atom (cysteine) prevents undersirable intermolecular disulfide bond formation at the mutation site.

Acid-resistant FGF in accordance with the present invention has been found to be highly stable in acid environments, particularly when used in conjunction with one or more of the stabilizing agents discussed in more detail below. Native mammalian FGF and FGF which is modified to be acid-resistant are very low in toxicity.

The preferred route of administration will depend on a number of factors including the condition being treated and patient convenience. For example, when used to treat ulcerating wounds of the bladder which are induced, for example, by radiation treatment or chemotherapy, then the acid-resistant FGF composition may be administered by urethral catheter. In treating ulcerating wounds of the gastrointestinal tract, the preferred route of administration is oral, e.g. by tablet, capsule, lozenge or chewable gum. Other routes of administration for diseases of the gastrointestinal tract include rectal, by enema and parenteral.

Preparation of acid-resistant FGF for administartion is accomplished by conventional techniques. For example, tablets and capsules are prepared by employing additives such as pharmaceutiaclly acceptable carriers (e.g. lactose, corn starch, light silicic anhydride, microcrystalline cellulose, sucrose), binders (e.g. alpha-form starch, methylcellulose, carboxymethylcellulose, hydroxypropylcellulose, hydroxy-propylmethylcellulose, polyvinylpyrrolidone), disintegrating agents (e.g. carboxymethylcellulose calcium, starch, low substituted hydroxypropylcellulose), surfactants (e.g. Tween 80 (Kao-Atlas), Pluronic F68 (Asahi Denka, Japan); polyoxyethylene-polyoxypropylene copolymer)), antioxidants (e.g. L-cysteine, sodium sulfite, sodium ascorbate), lubricants (e.g. magnesium stearate, talc), and the like.

Rectal preparations are also prepared by conventional techniques, for example, by employing an oleaginous base such as a higher fatty acid glyceride (e.g., cacao butter of the natural origin, Witepsols (a semisynthetic base, (Dynamite Nobel, Federal Republic of Germany)), a medium fatty acid glyceride (e.g. Miglyols (Dynamite Nobel)) or a vegetable oil (e.g., sesame oil, soybean oil, corn oil, cottonseed oil, olive oil).

When the composition is formulated into an injectable aqueous solution, the solution is prepared by conventional methods using a solvent such as an aqueous solvent (e.g., distilled water, physiological saline, Ringer's solution), or oily solvent (e.g., sesame oil, olive oil). If desired, one or more additives may be employed. Such additives include a dissolution aid (e.g. sodium salicylate, sodium acetate), buffer (e.g., sodium citrate, glycerine), isotonizing agent (e.g., glucose, invert sugar), stabilizers (e.g., human serum albumin, polyethylene glycol), preservatiave (e.g., benzyl alcohol, phenol) or analgesics (e.g., benzalkonium chloride, procaine hydrochloride).

When the composition is formulated into a solid preparation for injection, the preparation can be produced by routine methods using, for example, a diluent (e.g., distilled water, physiological saline, glucose), excipient (e.g., carboxymethylcellulose (CMC), sodium arginate), preservative (e.g., benzyl alcohol, benzalkonium chloride, phenol), or analegesics (e.g., glucose, calcium gluconate, procaine hydrochloride).

The dosage of acid-resistant FGF required is remarkably small when compared to other pharmaceutical agents such as the H₂-blockers, and depends on a number of factors including the condition being treated, whether or not it is used alone or in conjunction with stabilizing agents, antisecretory agents, cytoprotective agents and antacids, and the amount of food intake by the patient.

For example, when used to treat ulcerating diseases of the gastrointestinal tract in human adult patients, the amount of the acid-resistant FGF protein component of the composition to be administered orally is generally from about 0.1 μg to 30 mg per day, preferably from about 0.1 μg to 10 mg, more preferably from about 1.0 μg to 3 mg per day, and most preferably from about 10 μg to 300 μg per day. For oral administration, 10 μg to 150 μg of the rhbFGF mutein CS23 or its salt may be formulated as a tablet or a capsule together with a pharmaceutically acceptable carrier, diluent or other suitable vehicle. Such a formulation is beneficially administered one to four times daily to bring the dosage within the preferred range.

For certain diseases of the lower gastrointestinal tract such as peptic ulcers and ulcerated colitis, it is preferred that the acid-resistant FGF composition be coated with an enteric copolymer such as hydroxypropylmethylcellulose phthalate, cellulose acetate phthalate or a methacrylic acid copolymer to further protect the acid-resistant FGF from acid and digestive enzymes such as pepsin. This coated composition thus passes into the gastrointestinal tract such as the digestive tract and alimentary canal where its therapeutic value is optimized.

In accordance with another aspect of the present invention, it has been found that certain agents further stabilize and/or potentiate the activity of acid-resistant FGF. Such agents include antisecretory agents, cytoprotective agents, antacids, and stabilizing agents such as glycosaminoglycans and a group of compounds known as glucan sulfates. As the skilled artisan will appreciate, the relative amount of such stabilizing-/potentiating agents to FGF may vary depending on a number of factors, including the agent used, patient's condition and administration route. In general, the ratio of such stabilizers to FGF by weight is between about 0.1 to 100, preferably 0.2 to 20, more preferably from about 0.5 to 4.

The preferred antisecretory agents are ranitidine and cimetidine. The amount of antisecretory agent used will vary in accordance with the above-described factors. For example, when used to treat peptic ulcers, one preferred composition includes from about 10 to 300 μg, preferably about 100 μg of the rhbFGF CS23 mutein and from about 20 to 600 mg, preferably about 200 mg of the antisecretory agent.

The preferred antacids include aluminum hydroxide gel, sodium bicarbonate and sucralfate. The antacid may be taken in conjunction with the acid-resistant FGF or may be incorporated as one component of the acid-resistant FGF composition itself. The amount of antacid will generally be 0.5 to 5 g per treatment.

The amount of cytoprotective agent used will depend on a number of factors including the agent used. For the prostaglandin derivative the amount is generally between 2.5 to 5 μg per adult human, and in the case of spizofurone about 80 mg per adult human.

Stabilizing agents which may be used in accordance with the present invention include glycosaminoglycans such as heparin, fragments of heparin, glucan sulfates such as dextran sulfate, cyclodextrin sulfate and β-1,3-glucan sulfate. Said glucan sulfate preferably has a sulfur content of not less than about 3% (w/w), more preferably between about 12 to 20% (w/w), and most preferably between about 16 to 20% (w/w). The preferred stabilizing agents are the glucan sulfates, and in particular dextran sulfate.

Glycosaminoglycan, has been previously described, for example, in Molecular Biology of the Cell, Garland Publishing Inc., New York, London, 1983. It is desirable that the glycosaminoglycan used in the present invention have about 0.1 to 3.0 sulfate groups per disaccharide unit, and that its molecular weight be in the range of from 1,000 to 100,000, preferably from 2,000 to 50,000. Examples of such glycosaminoglycans include heparin, heparan sulfate and dermatan sulfate.

Heparin is described, for example, in the Merck Index, 8th ed. 1983. The molecular weight of heparin ranges from about 5,000 to about 40,000.

Cyclodextrins are natural cyclic compounds consisting of six (alpha), seven (beta) or eight (gamma) D-glucose units linked by alpha(1->4) linkage. They have a donut-shaped molecular structure which provides a cavity whereby clathrates may form with guest molecules of suitable size.

Cyclodextrin sulfate is an ester resulting from the sulfonation of these cyclodextrins. Sulfonation is achieved by known methods. One preferred method of sulfonation is described in U.S. Pat. No. 2,923,704 and Japanese Patent Application Laid-open No. 22/1975.

The sulfur content of cyclodextrin sulfate normally exceeds about 3% (w/w), and is preferably between about 12 to 24% (W/w). Such cyclodextrin sulfates are also very soluble in water.

The degree of sulfonation of cyclodextrin sulfate for the present invention may be at any level exceeding 12% (w/w) as calculated as sulfur content. Cyclodextrin sulfate containing about 16 to 21% (w/w) sulfur is particularly advantageous.

The alpha, beta, and gamma cyclodextrin sulfate salts are all usable as stabilizing agents r,f FGF protein component in accordance with the present invention. β-cyclodextrin salts such as beta-cyclodextrin tetradecasulfate are preferred.

β-1,3-glucan sulfate used in the present invention is produced by sulfonating β-1,3-glucan. β-1,3-glucan is produced by microorganisms belonging to the genus Alcaligenus or Agrobacterium, has straight chains, is water-soluble and is thermogelable. Processes for purifying various glucans are described in Ebisu et al., Journal of Bacteriology pp. 1489–1501, 1975.

Curdlan (also known as thermogelable polysaccharide PS, commercially available from Wako Pure Chemical Industries, Ltd. Japan) is known to be a water-insoluble, thermogelable, unbranched straight chain glucan which has β-(1->3) linkage alone and which is produced by microbial strains belonging to the genus Alcaligenes or Agrobacterium (see e.g., Japanese Patent Publication Nos. 7,000/1968, 32,673/1973 and 2,674/1973 and British Patent No. 1,352,938). The curdlan producers *Alcalioenes faecalis* var. *myxogenes* NTK-u strain, *Agrobacterium radiobacter* strain and *Agrobacterium radiobacter* U-19 strain are listed respectively under ATCC-21680, ATCC-6466 and ATCC-21679 in the American Type Culture Collection Catalogue of Strains, I, 15th edition, 1982.

Hydrolysates which are low molecular weight derivatives of curdlan may also be used. The method of its production is described in detail in Japanese Patent Application Laid-open No. 83798/1980, or in U.S. Pat. No. 4,454,315.

$\beta$-1,3-glucan may have an average degree of polymerization ($\overline{DP}$) below 1000. In particular, its partial hydrolysate with a $\overline{DP}$ ranging from 6 to about 300 is recommended, and its partial hydrolysate with a DP from 15 to about 200 is preferred.

The sulfate of straight chain $\beta$-1,3-glucan for the present invention is an ester resulting from the sulfonation of the hydroxyl groups of $\beta$-1,3-glucan or its lower polymers; an ester with an average degree of substitution ($\overline{DS}$) of 0.5 to 3 per monosaccharide unit is normally used, and an ester with a $\overline{DS}$ of 1 to 2 is preferably used.

Sulfonation of straignt chain $\beta$-1,3-glucan or its low molecular weight polymer can be achieved by the method described in Journal of Biological Chemistry, 239, 2986 (1964). The sulfur content of $\beta$-1,3-glucan sulfate is normally over 5% (W/W), preferably about 10 to 21% (W/W), and it is very soluble in water.

Examples of the preferred glucan sulfate, dextran sulfate, employable in the present invention include sulfate of dextran, the dextran being produced from sucrose by the action of microorganisms such as *Leuconostoc mesenteroides*.

Dextran sulfate is a partial sulfate of dextran whose principal structure is an alpha (1->6) linkage of glucose, and the sulfur content is usually not less than about 12%, preferably about 16 to 20%. The average molecular weight is in the range of from about 1,000 to 40,000,000, preferably in the range of from about 3,000 to 1,000,000 and the dextran sulfate is very soluble in water.

The glucan sulfate employable in the present invention may also be in the form of a salt. As the salt, any pharmaceutically acceptable cation may be employed, e.g., sodium, potassium, ammonium, trimethyl ammonium, and the like.

When bringing glucan sulfate into contact with the FGF protein component in an aqueous medium, it may be conducted by first adding glucan sulfate in the free state then by adding an adequate amount of an alkali or an acid to adjust the pH desirably. By the addition of an alkali, the glucan sulfate may take the form of a salt in the aqueous medium, or a mixture of free glucan sulfate and glucan sulfate in the salt form may co-exist.

When the FGF protein component of the present invention is brought into contact with glucan sulfate in an aqueous medium, it is preferably conducted in the presence of di- or tri-basic carboxylic acid to give an even more stabilized FGF. Examples of di-basic carboxylic acid include tartaric acid, maleic acid, malic acid, fumaric acid, etc. Examples of tri-basic carboxylic acid include citric acid, iso-citric acid, etc.

The above-mentioned carboxylic acids may also be in the form of a salt. It may also be possible that native carboxylic acid be added to an aqueous medium, to which is added an adequate amount of an alkali or an acid to adjust the pH desirably. By the addition of an alkali, the glucan sulfate may take the form of a salt in the aqueous medium, or a mixture of free glucan sulfate and glucan sulfate in the salt form may co-exist.

When FGF protein component is brought into contact with glucan sulfate in an aqueous medium, the ratio of glucan sulfate to the FGF protein component ranges from about 0.1 to 100 by weight, preferably from 0.2 to 20 by weight most preferably from 0.5 to 4 by weight.

The concentration of glucan sulfate in an aqueous medium ranges preferably from about 0.0005 to 5 w/v %, more preferably from about 0.01 to 1 w/v %. The concentration of acid-resistant FGF in an aqueous medium ranges preferably from about 0.0005 to 5 w/v %, more preferably from about 0.01 to 1 w/v %. The amount of the carboxylic acid is preferably such as its concentration in an aqueous medium ranges from 1 mM to 1M, more preferably from about 10 mM to 500 mM.

For bringing the FGF protein component into contact with glucan sulfate and further with carboxylic acid in an aqueous medium, mere mixing of these materials in the aqueous medium accomplishes the purpose.

As the aqueous medium, use is preferably made of distilled water, physiological saline, glucose solution, buffers such as phosphate buffer and Tris-hydroxymethyl-aminomethane-HCl buffer.

An aqueous solution of FGF protein component, an aqueous solution of glucan sulfate and an aqueous solution of carboxylic acid may be mixed or a mixture of these materials in solid form may be dissolved in water. The mixing of these materials is conducted at temperatures ranging from 0° to 40° C. and preferably at pH ranging from about 3 to 10, more preferably from about 5 to 9. The time required for mixing is usually in the range of from about 1 to 30 minutes. The resulting composition may be lyophilized, during which procedure a complex may be formed and recovered.

For separating and recovering resulting stabilized FGF composition, a gel-filtration method using Sephadex gel, etc. or an ion-exchange chromatography using DEAE- or CM- Toyopearl may be used. Alternatively, the stabilized FGF composition can be used as it is, without separation or recovery.

By the processes described above, a highly stabilized composition of FGF is obtained, which composition can be safely used to treat mammals such as humans, rats, guinea pigs, dogs, mice, and the like.

The invention will be further illustrated with reference to the following examples which will aid in the understanding of the present invention, but which are not to be construed as a limitation thereof.

The recombinant human basic FGF (rhbFGF) used in the following Examples 5, 6 and 7 was produced in the manner described in Example I, 3, 6 or 8 of EP-237,966 employing a transformant *Escherichia coli* K12 MM294/pTB669 (IFO 14532, FERM BP-1281).

rhbFGF mutein CS23 used in the following Examples 1, 2, 3, 5, 6 and 7 was produced by the manner described in Example 9, and in the above-referenced Biochemical and Biophysical Research Communications vol. 151, pages 701-708 (1988), and Reference Examples 1 and 2 and Examples 1, 6,7 and 24 of U.S. patent application Ser. No. 161,123 which corresponds to EP-281,822 A2 employing a transformant *Escherichia coli* MM294/pTB 762 (IFO 14613, FERM BP-1645).

Recombinant human acidic FGF (rhaFGF) used in the following Example 6 was produced by the manner of Example 4 mentioned below.

EXAMPLE 1

In the following experiments, the animal model described by S. Szabo, MD in the American Journal of Pathology, pages 273-276, 1978, was used to induce duodenal ulcers in normal rats. Specifically, cysteamine was given at a dose of 25 milligrams per 100 grams of body weight (BW) orally by intragastric lavage 3 times on the same day. Twenty-four hours later, approximately 10% of the rats died of a perforated ulcer. By day 3, a small abdominal incision was made in each rat to determine if a duodenal ulcer was present. Rats without any external evidence of duodenal ulcer, approximately 1–2% of the surviving rats, were eliminated from the study. Thus, all rats entering the study had ulcers, and were randomized in order to prevent bias.

All of the rats used in the study began with a body weight of approximately 160 grams. The following results were obtained from four groups of rats treated for 21 days and sacrificed. All measurements were taken at the time of sacrifice after 21 days of therapy.

Group I

No FGF Therapy

Four rats with ulcers received no FGF therapy. The incidence, depth and area of their ulcers were statistically similar to 50 other untreated rats in studies previously carried out.

```
Mean Ulcer depth*  = 1.625 (S.D. = 1.302; S.E.M. = 0.460)
Mean Area of Ulcers = 8.83 mm² (S.D. = 9.75 S.E.M. = 3.45)
Body Weight          189 g
                     176 g
                     177 g
                     180 g
                x =  182 g
```
*"Mean Ulcer Depth" as used herein means as follows:
1 = a few cells deep into the epithelium;
2 = below the mucosa and into the muscle cells;
3 = through the muscle layer; and
4 = penetrated (just prior to perforation).

Group II rhbFGF mutein CS23 10 nanograms

A second group of four rats received rhbFGF mutein CS23 at 10 nanograms per 100 grams of body weight orally, twice a day. This dose was adjusted for the weight of each animal, twice each week.

```
Mean Ulcer depth   = 1.00 (S.D. = 1.414; S.E.M. = 0.707)
Mean Area of Ulcers = 3.14 mm²
Body Weight          232 g
                     212 g
                     204 g
                     216 g
                x =  216 g
```

Group III rhbFGF mutein CS23 100 nanograms

A third group of four rats received rhbFGF mutein CS23 at 100 nanograms per 100 grams of body weight orally, twice a day. Again, this dose was adjusted for the weight of each animal, twice each week.

```
Mean Ulcer depth   = 0.25 (S.D. = 0.5; S.E.M. = 0.25)
Mean Area of Ulcers = 0.392 mm² (all ulcers completely
                       healed, except for one tiny ulcer
                       still healing in one rat)
Body Weight          198 g
                     205 g
                     254 g
                     215 g
                x =  218 g
```

Group IV rhbFGF mutein CS23 500 nanograms

A final group of five rats received rhbFGF mutein CS23 at 500 nanograms per 100 grams of body weight orally, twice a day. Once again, this dose was adjusted for the weight of each animal, twice each week.

```
Mean Ulcer depth   = 0.6 (S.D. = 1.342; S.E.M = 0.6)
Mean Area of Ulcers = 1.88 mm²
                     207 g
                     214 g
                     295 g
                     196 g
                     216 g
Body Weight     x =  208 g
```

As can be seen from the above data, orally administered acid-resistant rhbFGF mutein CS23 results in rapid healing of cysteamine-induced ulcers. Even the best combination of H-2 blockers produce results less than or equal to that obtained in the 10 nanogram/rhbFGF mutein CS23 group.

EXAMPLE 2 rhbFGF mutein CS23 was added to a Dulbecco MEM medium containing 10% fetal calf serum to obtain a concentration of 10 μg/ml, to which was further added a salt of dextran sulfate (from Seikagagu Kogyo, Japan) so that the final concentration of the latter was 25 μg/ml. This medium was incubated at 37° C. for 24 hours. The salts of dextran sulfate were sodium salts whose average molecular weight was 5,000, 7,500 or 500,000, respectively. As a control group, the same medium, to which no dextran sulfate sodium was added, was employed. The remaining activities after 24 hours are shown in Table 1. In the remaining control, no substantial mutein CS23 activity remained, while in the test groups, the FGF activity remained stable.

TABLE 1

| Additive | Remaining FGF activity (%) |
|---|---|
| Dextran sulfate sodium (average molecular weight 5,000) | 93 |
| Dextran sulfate sodium (average molecular weight 7,500) | 100 |
| Dextran sulfate sodium (average molecular weight 500,000) | 100 |
| Control | 6 |

From the above data, it can be seen that dextran sulfate protects the rhbFGF mutein CS23 from temperatures to which it would be exposed in treating mammals. In other words, by bringing dextran sulfate into contact with FGF in an aqueous medium, stabilized FGF can be obtained. This stabilized FGF can be formulated into pharmaceutical preparations which are resistant to heat, acid and enzyme reactions found in the gastrointestinal tract.

EXAMPLE 3

An aqueous solution (pH 7.4) containing 0.5 mg of rhbFGF mutein CS23, 0.23 mg of dextran sulfate sodium having an average molecular weight 7500,and 15 mg of sodium citrate per ml was prepared.

EXAMPLE 4

Production of acidic FGF:

Human acidic FGF was produced by the manner mentioned below referring to the methods described in Biotechnology 5, 960 (1987), Journal of Biological Chemistry 263, 16471 (1988), and ICSU Short Report volume 8, Advances in Gene Technology: Protein Engineering and Production, Proceedings of the 1988 Miami Bio/Technology Winter Symposium, IRL Press, page 110.

(i) Construction of expression plasmid:

The cDNA (FIG. 1), which codes for human acidic FGF, was chemically synthesized and inserted into a plasmid pUC18 (Methods in Enzymology, 101, 20-78 (1983)) to give plasmid pTB917. The plasmid pTB917 was cleaved with BspMI and the ends were blunted by the reaction of E. coli DNA polymerase I large fragment. Then, the DNA was digested with BamHI to give 0.45 Kb DNA fragment. As a vector DNA, pET3c (Studier, F. W. et al. Journal of Molecular Biology, 189, 113-130 (1986)) which carries $\phi$10 promoter of T7 phage was employed. PET3c was cleaved with NdeI, and blunted by employing E. coli DNA polymerase I large fragment. Thereafter, the NcoI linker 5'-CCATGG-3' was ligated to this DNA using T4 DNA ligase. The resulting plasmid was cleaved with NcoI, blunted with E. coli DNA polymerase I large fragment, and thereafter cleaved with BamHI to remove S10 sequence. To that site the 0.45Kb BspMI-BamHI blunt-ended fragment was inserted by ligation with T4 DNA ligase to give plasmid pTB 975 (FIG. 2).

(ii) Expression of haFGF cDNA in E. coli:

Escherichia coli MM294 was lysogenized with lambda phage DE3 (Studier, supra), in which the RNA polymerase gene of T7 phage had been recombined. Thereafter, the plasmid pLysS was introduced into E. coli MM294 (DE 3) to give E. coli MM294 (DE3)/pLysS. To this strain, plasmid pTB975 was introduced, whereby E. coli MM294 (DE3)/pLysS, pTB975 was obtained. The above transformant was cultivated in L-broth containing 35 μg/ml of ampicillin and 10 μg/ml of chloramphenicol at 37° C. When the Klett value was about 170, isopropyl β-D-thiogalactoside (IPTG) was added to the medium to 0.5 mM as the final concentration, and the cultivation was continued for a further 3 hours. The cells were harvested by centrifugation, washed with PBS, harvested again, and stored at −20° C.

Figure 3:
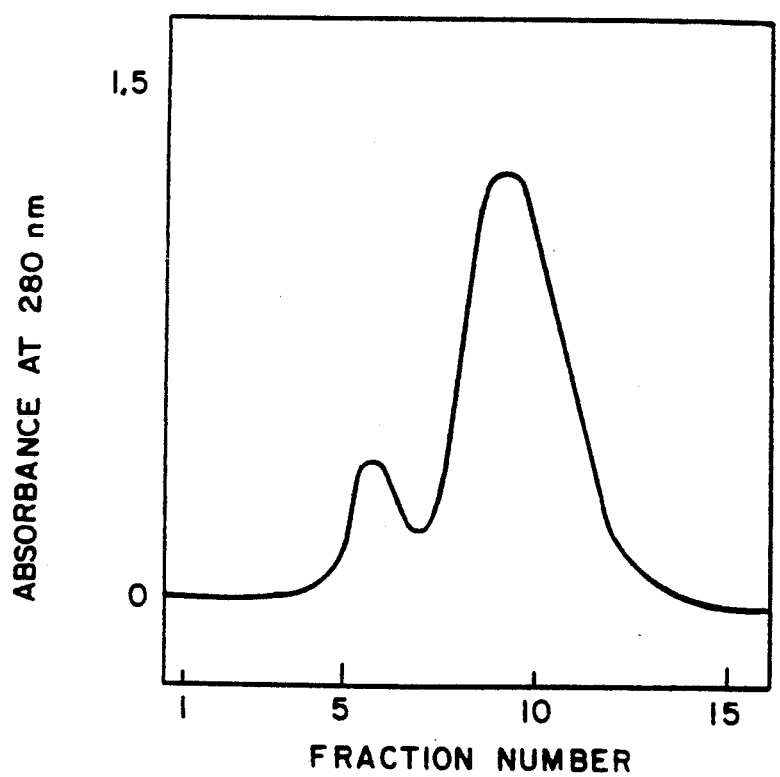
FIGS. 3 to 5 show the elution patterns of the human acidic FGF in Example 4.
Figure 4:
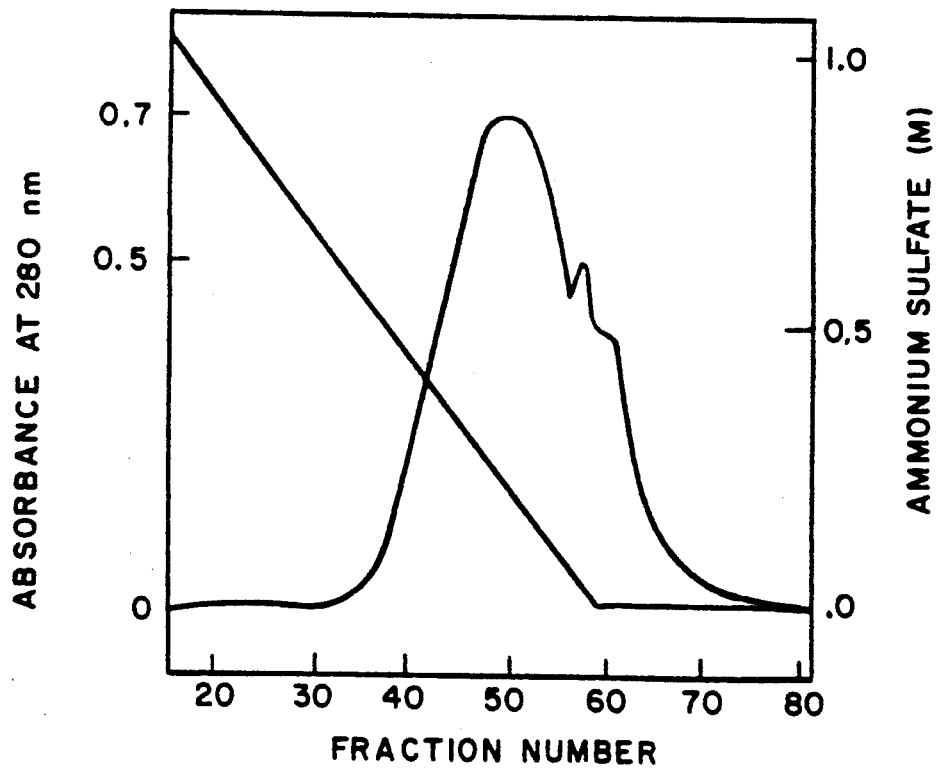

(iii) Purification of haFGF:

The cells collected from 1 liter of cultured broth were suspended in 100 ml of buffer containing 10 mM Tris-HCl (pH7.4), 10 mM EDTA, 0.6 M NaCl, 10 % sucrose and 0.25 mM PMSF and then to the suspension egg white lysozyme was added at a concentration of 0.5 mg/ml. After keeping in an ice-bath for one hour, the mixture was incubated at 37° C. for 5 minutes, subjected to ultrasonication (20 seconds, twice), and subjected to centrifugation (SORVALL, 18000 rpm, 30 min., 4° C.) to give a supernatant. This supernatant was mixed with buffer containing 20mM Tris-HCl (pH7.4) and 1mM EDTA under ice-cooling. The resulting mixture was passed through a heparin Sepharose column (diameter 2.5×4 cm) equilibrated with a buffer containing 20 mM Tris-HCl (pH 7.4), 1 mM EDTA, and 0.2 M NaCl. After washing the column with 150 ml buffer containing 20 mM Tris-HCl (pH 7.4), 1 mM EDTA and 0.5 M NaCl, protein was eluted with buffer containing 20 mM Tris-HCl (pH 7.4), 1 mM EDTA and 1.5 M NaCl. The eluates were fractionated to be 6 ml each, and the fractions (Nos. 8-11, total 24 ml) shown as the second peak were collected by monitoring with OD 280 (FIG. 3). To these fractions an equal amount of buffer (22 ml) containing 20 mM Tris-HCl (pH 7.4), 1mM EDTA and 2M (NHhd)$_2$SO$_4$ was added. The mixture was passed through a phenyl Sepharose column (diameter 2.5×8 cm) equilibrated with buffer containing 20 mM Tris-HCl (pH 7.4), 1 mM EDTA and 1M (NH$_4$)$_2$SO$_4$ at a flow rate 0.5 ml/min. After washing the column with the buffer of the same components employed for equilibration, elution was performed on a linear gradient of 1 M to 0 M ammonium sulfate (flow rate 0.5 m./min., gradient time 200 min.) The fractions Nos. 40-55 (FIG. 4) were collected to give pruified human acidic FGF.

Figure 5:
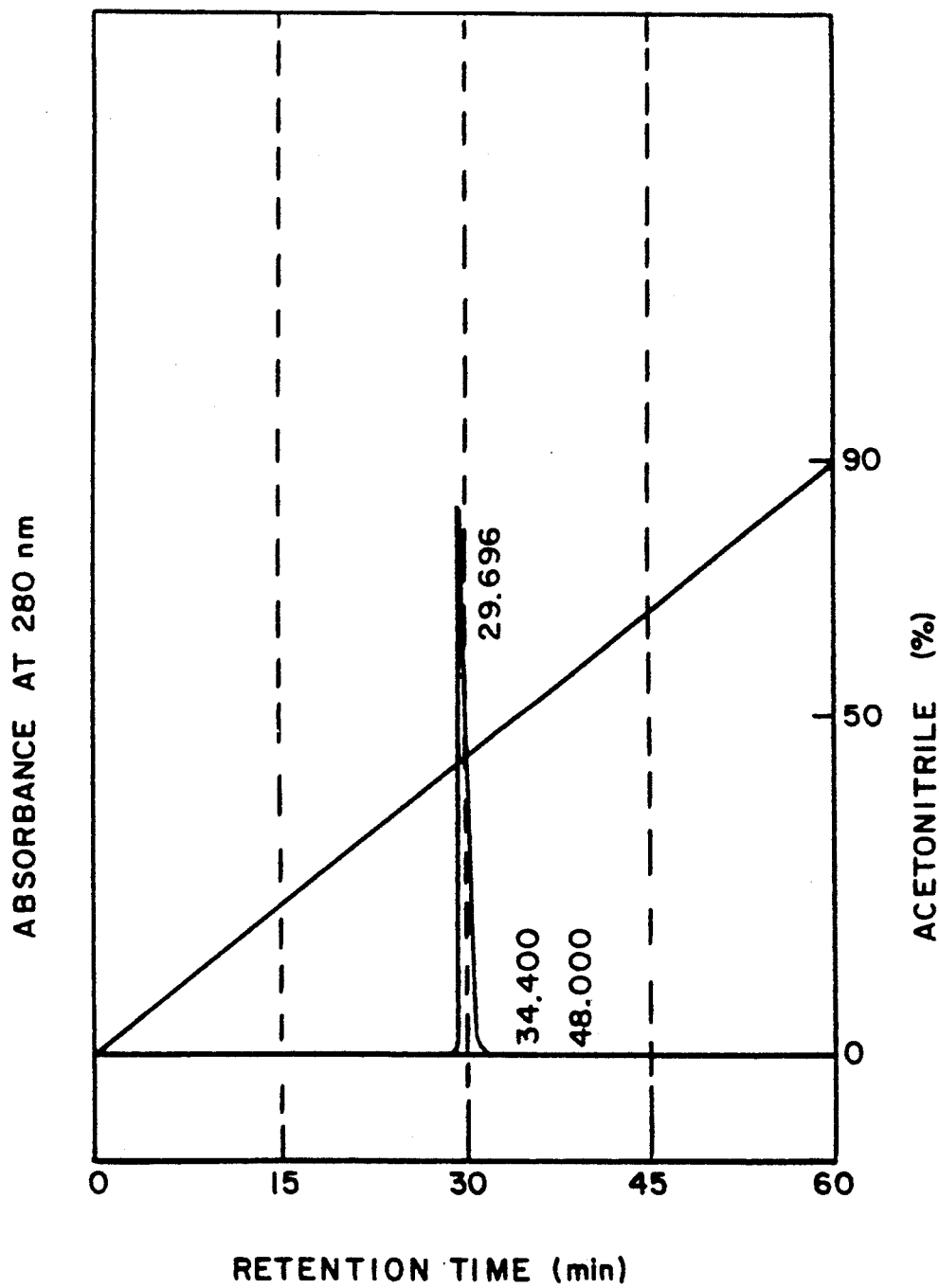

(iv) Reversed Phase C4 HPLC:

0.25 ml of 1.2 mg/ml solution containing the purified haFGF obtained in step (iii) was mixed with 0.1 % trifluoroacetic acid (TFA), and the mixture was applied to reversed phase C4 column (VYDAC, USA). Elution was performed on a linear gradient of 0% to 90% acetonitrile under the presence of 0.1 % TFA to investigate the elution pattern. Flow rate 1 ml/min. Gradient time 60 min. The results are shown in FIG. 5.

(v) Biological Activity

Biological activity of the purified haFGF obtained in step (iv) was measured by the method of Sasada et al. Mol. Cell Biol. 8, 588–594 (1988), namely the activity was measured by the incorporation of [3H] thymidine in DNA in BALB/c3T3 cell. When sample was added, a solution of heparin (SIGMA , Grade I) was admixed to the culture medium and the sample, when necessary.

EXAMPLE 5

In the following experiments, the animal model described by K. Takagi et al. Jpn. J. Pharmacol., 19 p.418–426, 1969, was used to induce gastric, duodenal, or colonic ulcers in normal rats. Seven-week old male Jcl:Sprague-Dawley rats weighing about 250 g were used. Rats were anesthetized with ether and an incision was made in the abdomen. A round metal mold, 6 mm in diameter, was placed in close contact with the serosal surface at the junction of the anterior wall of the corpus and antrum in the stomach, the duodenal wall, about 7 mm distal to pylorous, or the colonic wall, about 5 cm distal to the ileo-cecal junction. Glacial acetic acid (50 μl) was poured into the mold and was left in place for 20 seconds. After the acetic acid was removed, the treated surface was rinsed with 100 μl of saline and the abdomen was closed. The FGF compositions, suspended in 5% Gum arabic solution, were given orally twice a day (9 a.m. and 4 p.m.) for 6 consecutive days beginning the next day of the operation. The animals were sacrificed by CO$_2$ asphyxiation 7 days after the operation. The ulcerated areas (mm$^2$) and depth (grade 0 to about 3; 0: no lesion, 1: muoosal erosion, 2: moderate ulcer, 3: deep ulcer or perforation) were measured under a dissecting microscope with a 1 mm square grid eyepiece (x10).

The ulcer index was obtained from the product of area and depth.

Acetic acid applied to the serosal surface of the stomach, duodenum and colon produced a round ulcer. As can be seen from Tables 2-4, the ulcer indices of control group in each ulcer at 7 days after operation were 6.7±1.1, 5.7±1.1 and 14.2±1.6, respectively. The control group received the vehicle alone comprising 50 mM citrate buffer (pH 7.0) containing 150 mM NaCl; the rhbFGF group received rhbFGF orally at 30 μg per kg of body weight; the CS23 group received CS23 (rhbFGF mutein CS23) orally at 30 μg per kg of body weight; and the CS23-DS group received a mixture of CS23 and DS (dextran sulfate) with an average molecular weight of 7500 at 30 μg and 13.8 μg, respectively, per kg of body weight. CS23 and CS23-DS accelerated the healing of the gastric, duodenal, and colonic ulcers; the effects on the duodenal and colonic ulcer being statistically significant (Tables 2-4). The effect of rhbFGF on the healing of the ulcers was less significant less than CS23 and CS23-DS.

TABLE 2

Effects of rhbFGF, CS23 and CS23-DS on the healing process of acetic acid-induced gastric ulcers in rats.

| Treatment | Dose (μg/kg, p.o) | No. of rats | Ulcer index | % Improvement in ulcer index |
|---|---|---|---|---|
| Control | | 8 | 6.7 ± 1.1 | — |
| rhbFGF | 30 | 8 | 5.8 ± 0.9 | 13 |
| CS23 | 30 | 8 | 4.3 ± 0.9 | 36 |
| CS23-DS | 30 | 8 | 3.6 ± 0.9 | 46 |

Results are expressed as mean ± s.e.

TABLE 3

Effects of rhbFGF, CS23 and CS23-DS on the healing process of acetic acid-induced duodenal ulcers in rats

| Treatment | Dose (μg/kg, p.o) | No. of rats | Ulcer index | % Improvement in ulcer index |
|---|---|---|---|---|
| Control | | 8 | 5.7 ± 1.1 | — |
| rhbFGF | 30 | 8 | 5.9 ± 1.4 | −4 |
| CS23 | 30 | 8 | 2.5 ± 0.5* | 56 |
| CS23-DS | 30 | 7 | 1.7 ± 0.4** | 70 |

Results are expressed as mean ± s.e.
*p < 0.05, **p < 0.01 vs. Control (Student's t test)

TABLE 4

Effects of rhbFGF, CS23 and CS23-DS on the healing process of acetic-induced colonic ulcers in rats

| Treatment | Dose (μg/kg, p.o.) | No. of rats | Ulcer index | % Improvement in ulcer index |
|---|---|---|---|---|
| Control | | 8 | 14.2 ± 1.6 | — |
| rhbFGF | 30 | 8 | 14.0 ± 1.5 | 1 |
| CS23 | 30 | 8 | 8.0 ± 1.9* | 44 |
| CS23-DS | 30 | 8 | 7.3 ± 2.1 | 49 |

Results are expressed as mean ± s.e.
*p < 0.05 s. Control (Student's t test)

EXAMPLE 6

In the following experiments, colonic ulcers were induced by the topical application of N-ethylmaleimide (NEM) on the surface of colonic mucosa. Seven-week old male Jcl:Sprague-Dawley rats weighing about 250 g were used. Rats were administered 50 μl of 3% NEM dissolved in 1% methyl cellulose intracolonically 6 cm oral portion from the anus using a Nelaton's cathether. The FGF compositions dissolved in 50 mM citrate buffer (pH 7.0) containing 150 mM NaCl or 20 mM Tris-HCl buffer (pH 7.0) in a volume of 0.2 ml/rat were given intracolonally 7 cm from the anus using a Nelaton's cathether twice a day (9 a.m. and 4 p.m.) for 10 consecutive days beginning the day after inducement of the ulcer by NEM treatment. The animals were sacrificed by $CO_2$ asphyxiation 11 days after NEM treatment. The ulcerated area ($mm^2$) and depth (grade 0-3: 0: no lesion, 1: mucosal erosion, 2: moderate ulcer, 3: deep ulcer or perforation) were measured under a dissecting microscope with a 1 mm square grid eyepiece (×10). The ulcer index was obtained from the product of area and depth.

In Exp. 1, the control group received the vehicle alone comprising 50 mM citrate buffer (pH 7.0) containing 150 mM NaCl; the rhbFGF group received rhbFGF at 2 μg per rat; the CS23 group received CS23 at 2 μg per rat; and the CS23-DS group received a mixture of CS23 and DS with an average molecular weight of 7500 at 2 μg per rat and 0.92 μg per rat, respectively. In Exp. 2, the control group received 20 mM Tris-HCl buffer (pH 7.0) alone, rhaFGF group received rhaFGF prepared by the manner of Example 4 at 2 μg per rat.

As can be seen from Table 5, NEM applied to the mucosal surface of the colon produced severe deep ulcers. The ulcer index of control group 11 days after the administration of NEM was 231.6±51.1 in Exp. 1 and 191.6±84.5 in Exp. 2, respectively. All of rhbFGF, CS23, CS23-DS and rhaFGF and rhaFGF accelerated the healing of the colonic ulcers.

TABLE 5

Effects of rhbFGF, CS23, CS23-DS and rhaFGF on the healing process of NEM-induced colonic ulcers in rats

| Treatment | Dose (μg/rat) | No. of rats | Ulcer index | % Improvement in ulcer index |
|---|---|---|---|---|
| Exp. 1 | | | | |
| Control | | 8 | 231.6 ± 51.1 | — |
| rhbFGF | 2 | 9 | 167.6 ± 37.3 | 28 |
| CS23 | 2 | 9 | 108.4 ± 26.3* | 53 |
| CS23-DS | 2 | 9 | 79.4 ± 14.9* | 66 |
| Exp. 2 | | | | |
| Control | | 10 | 191.6 ± 84.5 | — |
| rhaFGF | 2 | 9 | 99.4 ± 25.2 | 48 |

Results are expressed as mean ± s.e.
*p < 0.05 vs. Control (Student's t test)

EXAMPLE 7

In the following example, the animal model described in Example 1 was used to induce duodenal ulcers in normal rats. Female rats received 3 doses of cysteamine-HCl 25 mg/100g p.o. Three days later rats with penetrating duodenal ulcers (as determined by laparotomy) were randomized into control and treatment groups. Rats (6-8/group) received (1) vehicle alone; (2) rhbFGF (wild) (wild type recombinant human bFGF); or (3) CS23 (acid-resistant mutein rhbFGF mutein CS23) at 100ng/100g by gavage twice daily until autopsy on day 21, when ulcers were measured and histologic sections taken. The experiment was repeated 3 times and the results pooled in Table 6:

TABLE 6

| Therapy | Rats with Ulcers | Ulcer Crater |
|---|---|---|
| Control | 89% | 9.8 ± 4.6 $mm^2$ |
| rhbFGF (wild) | 80% | 2.1 ± 1.3 $mm^2$ |
| | | (p = 0.073) |
| (CS23) | 33% | 1.7 ± 1.1 $mm^2$ |

TABLE 6-continued

| Therapy | Rats with Ulcers | Ulcer Crater |
|---------|------------------|--------------|
|         |                  | (p = 0.063)  |

As can be seen from Table 6, histology of FGF-treated rats revealed: prominent angiogenesis, mild mononuclear cell infiltration, and dense granulation tissue in the ulcer bed; healed ulcers which were completely epithelialized; hypertrophic normal gastric and duodenal mucosa. These fidings were not observed in the rats treated with vehicle alone.

EXAMPLE 8

In the following example, the animal model described in Examples 1 and 7 was used to induce duodenal ulcers in normal rats. Female rats received 3 doses of cysteamine-HCl 25 mg/100g p.o. Three days later rats with penetrating duodenal ulcers (as determined by laparotomy) were randomized into control and treatment groups. Rats (3-4/group) received (1) vehicle alone; (2) CS23 (acid-resistant mutein rhbFGF mutein CS23) at 100 ng/100g; and (3) cimetidine at 10 mg/100g by gavage twice daily until autopsy on day 21, when ulcers were measured and histologic sections taken. The results are shown in Table 7:

TABLE 7

| Therapy | Rats with Ulcers | Ulcer Crater |
|---------|------------------|--------------|
| Control | 100%             | 10.6 ± 9.0 mm² |
| Cimetidine | 50%           | 6.7 ± 2.9 mm² |
| (CS23)  | 75%              | 2.8 ± 1.9 mm² |

As can be seen from Table 7, use of the acid resistant FGF composition of the present invention in the treatment of ulcers results in marked improvement as compared with standard cimetidine therapy.

Other modifications of the above-described embodiments of the invention will be apparent to those skilled in the art and are intended to be within the scope of the following claims.

The following example is from the above-referenced EP 281.822 A2.

EXAMPLE 9

Reference Example 9.1

Construction of Plasmid Containing Gene Encoding Human bFGF (1) Isolation of cDNA-containing plasmid:

A cDNA whose host is *Escherichia coli* x1776 and which was prepared by incorporating a primary culture cell mRNA deriving from human prepuce in pCD vector [refer to Okayama, et al., *Molecular Cell Biology*, 3, 280 (1983)] was supplied by Dr. Okayama at the National Institute of Child Health and Human Development, Bethesda, USA. From this DNA was extracted a plasmid DNA by the alkali method [Birnboim, H.C. and Doly, J., *Nucleic Acids Research*, 1, 1513 (1979)], and this DNA was infected with *E. coli* DH1 to produce about $2 \times 10^6$ clones of a DNA library whose host is *E. coli* DH1.

Said cDNA library using *E. coli* DH1 was spread over 10 nitrocellulose filters (Millipore Inc., U.S.A. HATF filters) in an amount of about $5 \times 10^4$ clones/filter, whereafter a total of 20 replica filters in pairs were prepared using the above 10 filters as the master filters. *E. coli* cells on the replica filters were lysed with a 0.5N NaOH solution, and the exposed denatured plasmid DNA was immobilized to the filters [Grunstein, M. and Hogness, D. S., *Proc. Natl. Acad. Sci. USA* 72, 3961 (1975)].

Separately, based on the amino acid Nos. 13 to 20 (Pro-Pro-Gly-His-Phe-Lys-Asp-Pro) and amino acid Nos. 89 to 96 (Thr-Asp-Glu-Cys-Phe-Phe-Phe-Glu) on the amino acid sequence of bovine basic fibroblast growth factor as reported by F. Esch et al. [*Proc. Natl. Acad. Sci. USA*, 82, 6507 (1985)], the base sequences corresponding to these amino acid sequences were chemically synthesized. (For some codons, the 3rd letter was fixed arbitrarily. 5'GG A/G TC T/C TT A/G AA A/G TGGCCAGGAGG and 5'TC A/G AA A/G AA A/G AA A/G CA T/C TCGTCGGT, respectively. The underlined letters represent the fixed bases). For each of these oligonucleotides, reaction was carried out at 37° C. for 1 hour in 50 μl of a reaction liquid using T4 polynucleotide kinase (produced by Takara Shuzo Co., Ltd., Japan) [oligonucleotide 0.1 μg, 50 mM Tris-HCl pH 8.0 0.10 mM MgCl₂, 10 mM mercaptoethanol, 50 μCi gamma-$^{32}$P ATP (>5000Ci/mmole), 3 units of T4 polynucleotide kinase] to label the 5'-terminal of the oligonucleotides with $^{32}$p.

Using as probes the 2 oligonucleotides labeled in the above method, these were independently associated to a replica filter to which the DNA had been immobilized. Association reaction was carried out at 35° C. for 16 hours in a solution of 5×SSPE [180 mM NaCl, 10 mM NaH₂PO₄, 1 mM EDTA (pH 7.4)], 5×Denhardt's solution. 0.1% SDS and 100 μg/ml denatured salmon sperm DNA, containing 10 μCi of the probe. After the reaction, the filter was washed with a 0.1% SDS solution of 5×SSC [0.15M NaCl, 0.15M sodium citrate] at room temperature for 30 minutes 3 times, and then at 45° C. for 30 minutes 2 times [T. Maniatis et al., *Molecular Cloning*, Cold Spring Harbor Laboratory, p. 309 (1982)].

Radioautograms were taken from the washed filters, and strains responding to both probes were searched for by overlapping the 2 radioautograms from each pair of replica filters. By this method, 1 strain responding to both probes [*E. coli* K12 DH1/pTB627 (IFO 14494, FERM BP-1280)] was obtained from $5 \times 10^5$ clones.

(2) From the strain obtained in (1) above [*E. coli* K12 DH1/pTB627 (IFO 14494, FERM BP-1280)] was extracted and purified a plasmid DNA (pTB627) by the alkali method [*Nucleic Acids Research*, 1, 1513 (1979)].

Reference Example 9.2

Expression in *Escherichia coli* of gene which enclodes human bFGF (1) Construction of the plasmid pTB669 for human bFGF expression:

The plasmid pTB627 containing a human bFGF cDNA obtained in Reference Example 9.1(2) above was cleaved using the restriction enzymes AvaI and BalI to obtain a 0.44 kb DNA fragment containing the region coding for human bFGF. To the BalI cleavage site (blunt end) of this DNA fragment was ligated the BglII linker pCAGATCTG using T4 DNA ligase, and a 0.44 kb AvaI-BglII DNA fragment was separated. To this 0.44 kb AvaI-BglII DNA fragment T4 DNA ligase was reacted to ligate together the BglII cleavage sites, and this was followed by DNA polymerase (Klenow fragment) reaction in the presence of dXTP to blunt the AvaI cleavage sites. To this DNA fragment were ligated the synthetic oligonucleotides 5'AATTCTATG-CCAGCATTGC3' and 5'GCAATGCTGGCATAG3' after phosphorylation, using T4 DNA ligase, and this was followed by cleavage using EcoRI-BglII to prepare an about 0.46 kb DNA fragment. Separately, the DNA of plasmid ptrp781 [Kuokawa, T. et al., *Nucleic Acids Research*, 11, 3077–3085 (1983)], which has trp promoter, was cleaved using PstI, and was blunted by T4 DNA polymerase reaction. After ligation of the BglII linker pCAGATCTG to the blunt end by T4 DNA ligase reaction, cleavage using EcoRI-BglII was carried out to separate an about 3.2 kb DNA fragment containing trp promoter, the tetracycline resistance gene and a plasmid replication initiation site. The above-mentioned 0.46 kb EcoRI-BglII DNA fragment containing the gene region encoding human bFGF and this 3.2 kb DNA fragment were ligated together by T4 DNA ligase reaction to construct the plasmid pTB669 for human bFGF expression.

Using this plasmid pTB669, *E. coli* DH1 was transformed, whereby *E. coli* DH1/pTB669, which harbors the plasmid pTB669, was obtained.

In addition, using pTB669, *E. coli* K12 MM294 or C600 was transformed in the same manner as above, whereby *E. coli* K12 MM294/pTB669 (IFO 14532, FERM BP-1281) and *E. coli* C600/pTB669 were respectively obtained.

(2) Preparation of bacterial cell extracts:

Each of the above-mentioned transformants were cultured in an M9 medium containing 1% glucose, 0.4% casamino acid and 8 μm/ml tetracycline, and, when Klett value became about 200, 3β-indolylacrylic acid was added to a concentration of 25 g/ml, and this was followed by 4 more hours of cultivation. After cultivation, bacterial cells were collected, and were suspended in a 10% sucrose solution containing a 1/20 amount of 20 mM Tris-HCl (pH 7.6). To this suspension were added phenylmethylsulfonyl fluoride (PMSF) to 1mM, EDTA to 10 mM, Nacl to 0.1M, spermidine hydrochloride to 10 mM and lysozyme to 100 μg/ml (every figure shows the final concentration), and the mixture was left at 0° C. for 45 minutes, after which it was subjected to ultrasonication for 30 seconds. This solution was centrifuged at 18000 rpm (Sorval centrifuge, SS34 rotor) for 30 minutes to give a supernatant, which was used as a bacterial cell extract.

(3) Human bFGF activity of bacterial cell extracts:

Human bFGF activities are indicated by the weights of the standard sample of purified bovine brain FGF (produced by Takara Shuzo Co., Ltd.) in amounts equivalent to those of bacterial cell extracts in activity in growth promoting action on BALB/c3T3 cells.

Mouse BALB/c3T3 cells, in an amount of $2 \times 10^3$ cells per well, were inoculated to DMEM medium containing 5% calf serum on a Nunc 96-well microtiter plate (flat base) with each well containing 0.2 ml of the medium, and were cultured. Next day the medium was replaced with a DMEM medium containing 0.5% calf serum. After 3 days of cultivation, 10 μl of a bacterial cell extract, previously serially diluted in 5-fold steps with a DME medium containing 0.5% BSA, was added to each well, and was cultured. 20 hours later, 2 μl of $^3$H-Tdr (5 Ci/mmol, 0.5 mCi/ml RCC Amersham, UK) was added to each well. 6 hours later, cells were stripped by treatment with a phosphate-buffered solution (PBS) containing 0.2% trypsin-0.02% EDTA; and the cells were harvested onto a glass filter by means of a Titertech cell harvester, whereafter the amount of $^3$H-Tdr taken in the cells was determined using a scintillation counter. Using the same procedure, determinations were made of the activities of bovine brain FGF samples (produced by Takara Shuzo) of known weight. From the working curved thus obtained, calculations were made of the amounts of human bFGF in the bacterial cell extract samples. The results are shown in Table 8.

For control, the human bFGF productivity of the transformant *E. coli* DH1/ptrp781 obtained by transformation of *E. coli* DH1 using the plasmid ptrp781 was determined.

TABLE 8

| Transformant | Human bFGF Productivities Human bFGF Productivity (per liter of culture medium) |
|---|---|
| *E. coli* DH1/pTB669 | 2.95 mg |
| *E. coli* MM294/pTB669 | 23.15 |
| *E. coli* C600/pTB669 | 8.15 |
| *E. coli* DH1/ptrp781 | <0.0005 |

Example 9.1

Production of recombinant DNAs containing mutein-encoding base sequence (1) Cloning of M13 vector of human bFGF gene:

The plasmid pTB669 obtained in Reference Example 9.2 was digested with the restriction enzymes EcoRI and BamHI. The phage vector M13mp8 [J. Messing, *Methods in Enzymology*, 101, 20–78 (1983)] replicative-form (RF) DNA was digested with the restriction enzymes EcoRI and BamHI, and was mixed with the human bFGF DNA fragment deriving from the digested pTB669. The mixture was then ligated together by means of T4 DNA ligase; the ligated DNA was transformed into an infectable cell of the strain *E. coli* JM105; the resulting transformant was inoculated onto a plate using Xgal as an indicator [J. Messing, et al., *Nucleic Acids Research*, 9, 309–321 (1981)]; the plaque containing the recombinant phage (white plaque) was picked up; the base sequence of the recombinated region was determined by the dideoxynucleotide synthetic chain termination method [J. Messing et al., *Nucleic Acids Research* 9, 309 (1981)], whereby it was confirmed that human bFGF DNA had been accurately inserted.

From this M13-PO clone was purified a single-stranded phage DNA, which was then used as a template for site-directed mutagenesis using a synthetic oligonucleotide.

(2) Site-specific mutagenesis:

In the presence of 0.1 mM adenosine triphosphate (ATP), 50 mM Tris (hydroxymethyl)aminomethane hydrochloride (Tris-HCl), pH 8.0) 10 mM $MgCl_2$, 5 mM dithiothreitol (DTT) and 9 units of T4 kinase, in a total amount of 50 μl, 40 picomoles of the synthetic oligonucleotide:

5' > CGT TCT TGC TGT AGA GCC GCT < 3'

[primer for changing Cys 26 to Ser (the recognition sequence for the restriction enzyme RsaI disappears). (see FIG. 6)] was treated with T4 kinase at 37° C. of 1 hour. This kinase-treated primer (12 picomoles) hybridized to 5 μg of the single-stranded (ss) M13-PO DNA. The annealed mixture was then cooled on ice, and it was added to 50 μl of a reaction mixture containing 0.5 mM deoxynucleotide triphosphate (dNTP), 80 mM Tris-HCl (pH 7.4), 8 mM MgCl₂, 100 mM NaCl, 9 units of DNA polymerase I Klenow fragment, 0.5 mM ATP and 2 units of T4 DNA ligase, and reaction was carried out at 37° C. for 3 hours, and at 25° C. for 2 hours, whereafter the reaction was stopped by adding 2 µl of 0.2 mM EDTA. The reaction product was used to transform infectable JM 105 cells; the transformant cells thus obtained were allowed to grow overnight, whereafter an ssDNA was isolated from the culture medium supernatant. Using this SSDNA as a template for the 2nd cycle of primer elongation, gel-purified RF-type DNA was transformed into infectable JM 105 cells; the resulting transformant cells were spread over an agar plate, and were cultured overnight to obtain phage plaques.

(3) Site-directed mutagenesis:

The procedure of the above term (2) was repeated but the used synthetic oligonucleotide primer was:

5' > AAC GAT TAG CGC TCA CTC C < 3' which so changes the cysteine-70-encoding codon that the codon encodes serine. (A recognition sequence of the restriction enzyme HaeII was produced.) (See FIG. 6.)

(4) Site-directed mutagenesis:

The procedure of the above term (2) was repeated but the used synthetic oligonucleotide primer was:

5' > GTA ACA GAC TTA GAA GCT AGT < 3' which so changes the cysteine-88-encoding codon that the codon encodes serine. (A recognition sequence for the restriction enzyme AluI was produced). (See FIG. 6.)

(5) Site-directed mutagenesis:

The procedure of the above term was repeated but the synthetic oligonucleotide primer was:

5' > TCG AAG AAG AAA GAC TCA TCC < 3' which so changes the cysteine-93-encoding codon that the codon encodes serine. (A recognition sequence for the restriction enzyme HinfI was produced). (See FIG. 6.)

(6) Screening and identification of plaques made mutagenic:

Plates containing mutated M13-PO plaques [above term (1)] and 2 plates containing umutated M13-PO phage plaques were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl having a pH-value of 7.5 and 1.5M NaCl. The filters were twice washed on filters immersed in 2 x SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5 x SSC) having a pH-value of 7.0 containing 4 x Denhardt's solution (polyvinylpyrrolidone, Ficoll and bovine serum albumin, 1 x = 0.02%), 0.1% sodium dodecyl sulfate (SDS), 50 mM sodium phosphate-buffered solution having a pH-value of 7.0 and 100 µg/ml denatured salmon sperm DNA. Hybridization was carried out at 42° C. for 24 hours with 10⁵ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2 x SSC; the control filters, which contained umutated M13-PO plaques, were examined for radioactivity using a Geiger counter. While stepwise reducing SSC concentration, the control filters were washed until no detectable radioactivity remained on the filters. The minimum of the used SSC concentrations was 0.1 x SSC. The filters were allowed to dry in air, and autoradiographs were taken by 2 to 3 days of exposure at −70° C. Screening was carried out of 10,000 mutated M13-PO plaques and 100 unmutated control plaques using a kinase-treated oligonucleotide probe. None of the control plaques hybridized to the probe, while 3 to 10 of the mutated M13-PO plaques hybridized to the probe.

One of the mutated M13-PO plaques was taken, and was inoculated to a JM 105 culture medium. From the supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the TGC (Cys-26) codon had been changed to a TCT (Ser) codon; the TGT (Cys-70) codon, to an AGC (Ser) codon; the TGT (Cys-88) codon, to a TCT (Ser) codon; and the TGT-(Cys-93) codon, to a TCT (Ser) codon.

Of the mutated M13-PO phages, the phage in which the codon Cys-26 had become a Ser-encoding codon was names M13-P1; the phage in which the codon Cys-70 had become a Ser-encoding codon, M13-P2; the phage in which the codon Cys-88, M13-P3; and the phage in which the codon Cys-93 had become a Ser-encoding codon, M13-P4.

Example 9.2

Expression in *E. coli* of gene which encodes human bFGF mutein (1) The M13-P1 replicative form (RF) obtained in Example 9.1 above was cleaved using the restriction enzymes EcoRI and PstI to obtain about 0.5 kb DNA fragment containing the region encoding human bFGF mutein.

Figure 8:
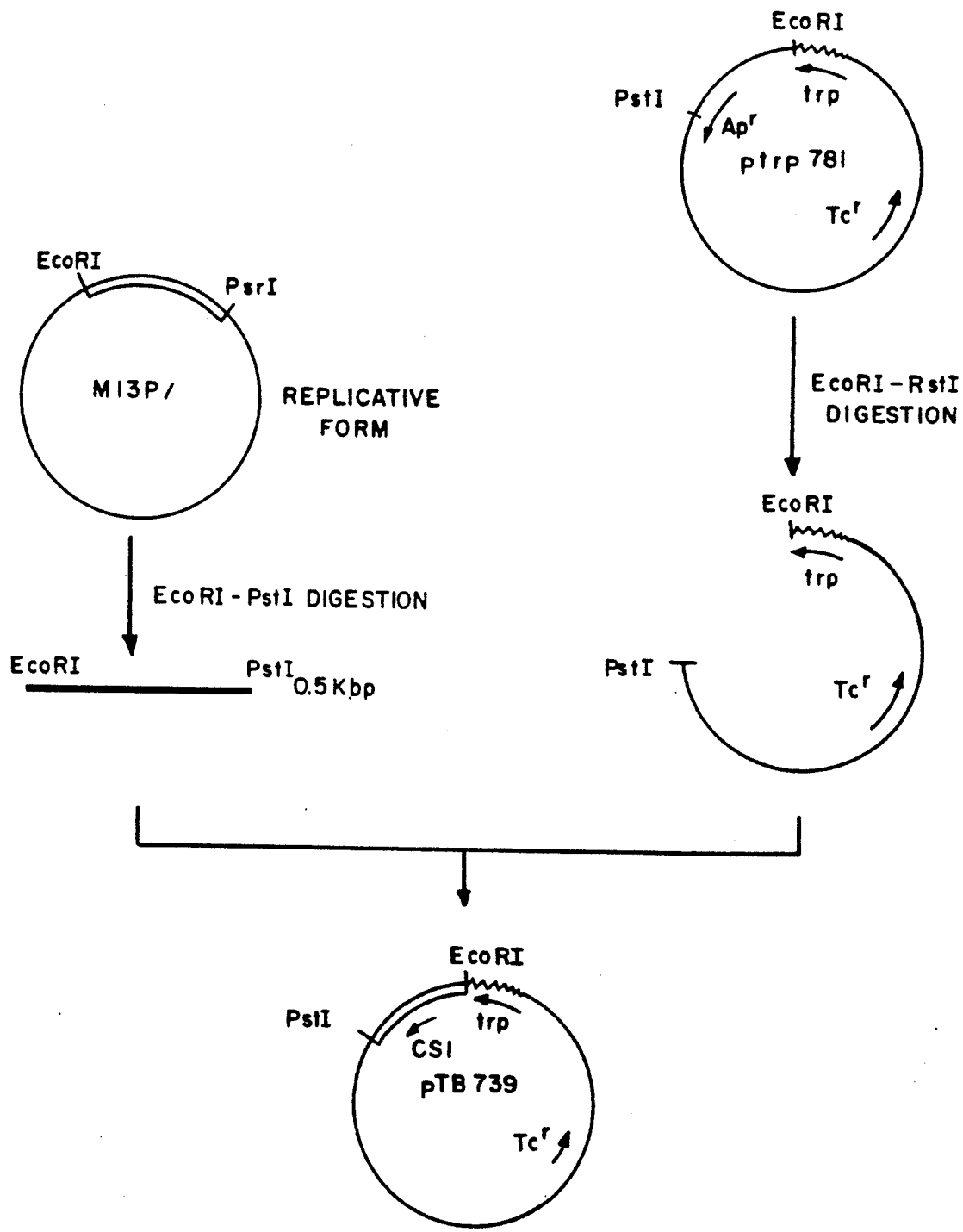
FIG. 8 shows the construction scheme of the plasmid pTB739 in Example 9.2(1).

Separately, the plasmid ptrp781 [Kurokawa, T. et al., *Nucleic Acids Research*, 11, 3077-3085 (1983)] DNA containing a trp promoter was cleaved using EcoRI-PstI to separate an about 3.2 kb DNA fragment containing a trp promoter, a tetracycline resistance gene and a plasmid replication initiation site. The above-mentioned 0.5 kb EcoRI-PstI DNA fragment containing the gene region encoding human bFGF mutein and this 3.2 kb DNA fragment were ligated together by T4 DNA ligase reaction to construct the plasmid pTB739 for human bFGF mutein expression (FIG. 8).

Using this plasmid pTB739, *E. Coli* DH1 was transformed, whereby the strain *E. coli* DH1/pTB739 (IFO 14575, FERM BP-1641) was obtained, which harbors the plasmid pTB739 containing the mutein-encoding gene shown in FIG. 7.

(2) Preparation of bacterial cell extract:

The above-mentioned transformant was cultured in an M9 medium containing 1% glucose, 0.4% casamino acid and 8 μg/ml tetracycline, and, when Klett value became about 200, 3β-indolylacrylic acid was added to a concentration of 25 μg/ml, and this was followed by cultivation for 4 more hours. After cultivation, bacterial cells were collected, and were suspended in a 10% sucrose solution containing a 1/20 amount of 20 mM Tris-HCl (pH 7.6). To this suspension were added phenylmethylsulfonyl fluoride (PMSF) to 1 mM, EDTA to 10 mM, NaCl to 0.1M, spermidine hydrochloride to 10 mM and lysozyme to 100 μg/ml (every figure shows the final concentration), and the mixture was left at 0° C. for 45 minutes, after which it was subjected to ultrasonication for 30 seconds. This solution was centrifuged at 18,000 rpm (Sorval centrifuge, SS34 rotor) for 30 minutes to give a supernatant, which was then used as a bacterial cell extract.

(3) Human bFGF activity of the bacterial cell extract:

Mouse BALB/c3T3 cells, in an amount of $2 \times 10^3$ cells per well, were inoculated to a DMEM medium containing 5% calf serum on Nunc-96-well microtiter plate (flat base) with each well containing 0.2 ml of the medium, and were cultured. Next day the medium was replaced with a DMEM medium containing 0.5% calf serum. After 3 days of cultivation, 10 μl of the bacterial cell extract, previously serially diluted in 5-fold steps with a DME medium containing 0.5% BSA, was added to each well, and was cultured. 20 hours later, 2 μl of $^3$H-Tdr (5 Ci/mmol, 0.5 mCi/ml RCC Amersham) was added to each well. 6 hours later, cells were stripped by treatment with a phosphate-buffered solution (PBS) containing 0.2% trypsin-0.02% EDTA, and the cells were harvested onto a glass filter by means of a Titertech cell harvester, whereafter the amount of $^3$H-Tdr taken in the cells was determined using a scintillation counter.

As a result, the bacterial cell extract from E. coli DH1/pTB739 exhibited FGF activity.

The mutein CS1, in which Cys at the 26-position of human bFGF had been replaced by Ser, was thus obtained.

Example 9.3

Screening and identification of plaques which were made mutagenic

Plates containing mutated M13-P2 phage plaques obtained in Example 9.1 and 9.2 plates containing umutated M13-P2 phage plaques obtained in Example 9.1 were cooled to 4° C., and the plaque from each plate was transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tri-HCl (pH 7.5) and 1.5M NaCl. The filters were twice washed on filters immersed in 2 x SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5 x SSC) having a pH-value of 7.0 containing 4 x Dehardt's solution (polyvinylpyrrolidone, Ficoll and bovine serum albumin, 1 x=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2 x SSD; the control filters, which contained umutated M13-P2 plaques, were examined for radioactivity using a Geiger counter. While stepwide reducing SSC concentration, the control filters were washed until no detectable radioactivity remained on the filters. The minimum of the used SSC concentrations was 0.1 x SSC. The filters were allowed to dry in air, and radioautographs were taken by 2 to 3 days of exposure at −70° C. Screening was carried out of 10,000 mutated M13-P2 plaques and 100 unmutated control plaques using a kinase-treated oligonucleotide probe. None of the control plaques hybridized to the probe, while 3 to 10 of the mutated M13-P2 plaques hybridized to the probe.

One of the mutated M13-P2 plaques were taken, and was inoculated to a JM105 culture medium. From the resulting supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the TGC (Cys-26) codon had been changed to a TCT (Ser) codon; the TGT (Cys-88), to a TCT (Ser) codon; and the TGT (Cys-93) codon to a TCT (Ser) codon.

Of the mutated M13-P2 phages, the phage in which the codons Cys-26 and -70 had become Ser-encoding codons was named M13-P12; the phage in which the codons Cys-70 and -88 had become Ser-encoding codons, M13-P23; and the phage in which the codons Cys-70 and -93 had become Ser-encoding codons, M13-P24.

Example 9.4

Figure 10:
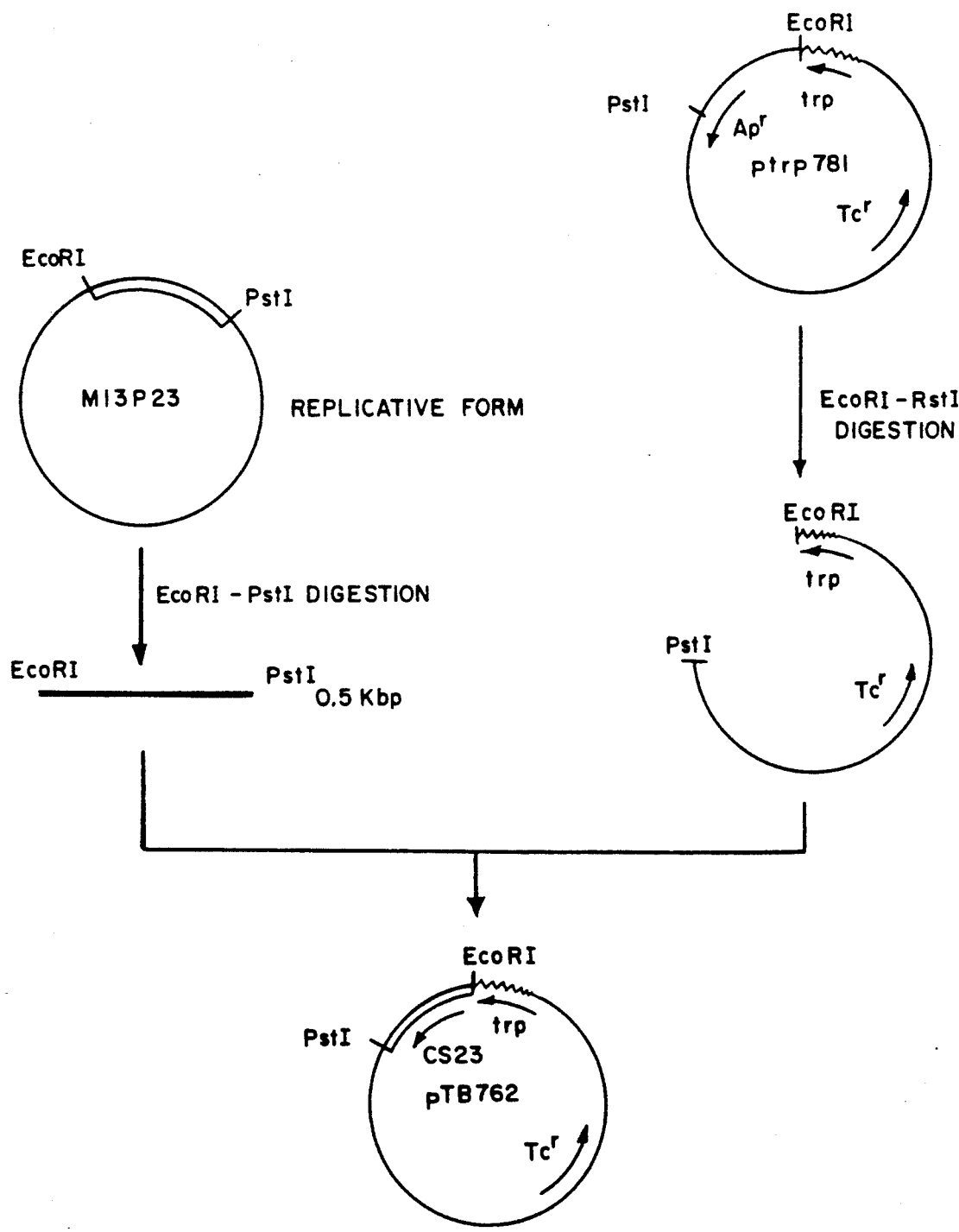
FIG. 10 shows the construction chart of the plasmid pTB762 in Example 9.4(1).

Expression of E. coli of gene encoding human bFGF mutein (1) Construction of the plasmid pTB762 for human bFGF mutein expression:

The M13-P23 replicative form (RF) obtained in Example 9.3 above was treated in the manner described in Example 9.2(1) to construct the plasmid pTB762 for human bFGF mutein expression (FIG. 10).

Using this plasmid pTB762, E. coli MM294 was transformed, whereby the strain E. coli MM294/pTB762 (IFO 14613, FERM BP-1645) was obtained, which harbors the plasmid pTB762 containing the muteinencoding gene shown in FIG. 9.

(2) Preparation of bacterial cell extract:

The above-mentioned transformant was cultured by the method described in Example 9.2(2) to give a supernatant, which was then used as a bacterial cell extract.

(3) Human bFGF activity of the bacterial cell extract:

A determination was made of the human bFGF activity of the bacterial cell extract obtained in (2) above, by the method described in Example 9.2(3).

As a result, the bacterial cell extract from E. coli MM294/pTB762 exhibited FGF activity.

The mutein CS23, in which Cys at the 70-position and at the 88-position had been replaced by Ser, was thus obtained.

Example 9.5

Purification of hbFGF mutein

Transformants producing respective muteins were cultured by the method described in Reference Example 9.2, whereby bacterial cell extracts were prepared. 25 ml of each extract (prepared from 500 ml of the culture medium) was passed through a column ($\phi 2 \times 10$ cm) of DEAE cellulose (DE52, Wattman, Inc., United Kingdom) equilibrated with a solution containing 20 mM Tris-HCl having a pH-value of 7.4 and 0.2M NaCl, whereby the nucleic acid constituents in the extract were removed. The effluent from the column and the washings resulting from the washing of the column with a solution containing 20 mM Tris-HCl having a pH-value of 7.4 and 0.2M NaCl were combined and collected (DEAE effluent fraction, 60 ml).

This fraction was subjected to high performance liquid chromatography using a high performance liquid chromatograph (Gilson, Inc., France) loaded with a Shodex AF-pax HR-894 heparin column (8 mm ID $\times$ 5 cm, produced by Showa Denko, Japan). After washing the column with a 20 mM Tris-HCl solution having a pH-value of 7.4, and then with a solution containing 20 mM Tris-HCl having a pH-value of 7.4 and 0.5M NaCl, linear gradient elution was carried out with the NaCl gradient of from 0.5M to 2M (60 ml volume, 1.0 ml/min. flow rate) in a buffer containing 20 mM Tris-HCl having a pH-value of 7.4.

Figure 11:
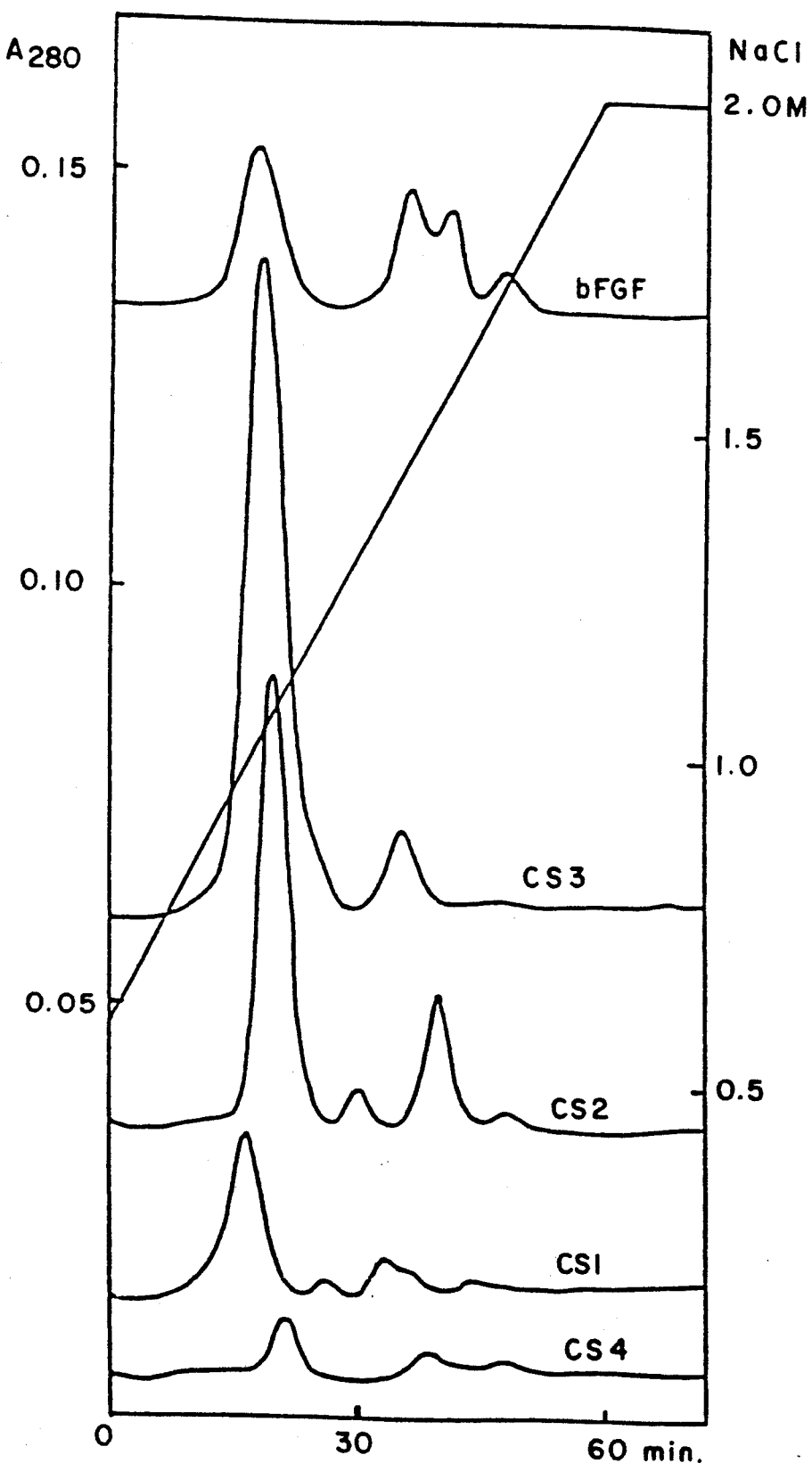
FIGS. 11 to 13 show the high performance liquid chromatography elution patterns of the muteins obtained in Example 9.5.
Figure 12:
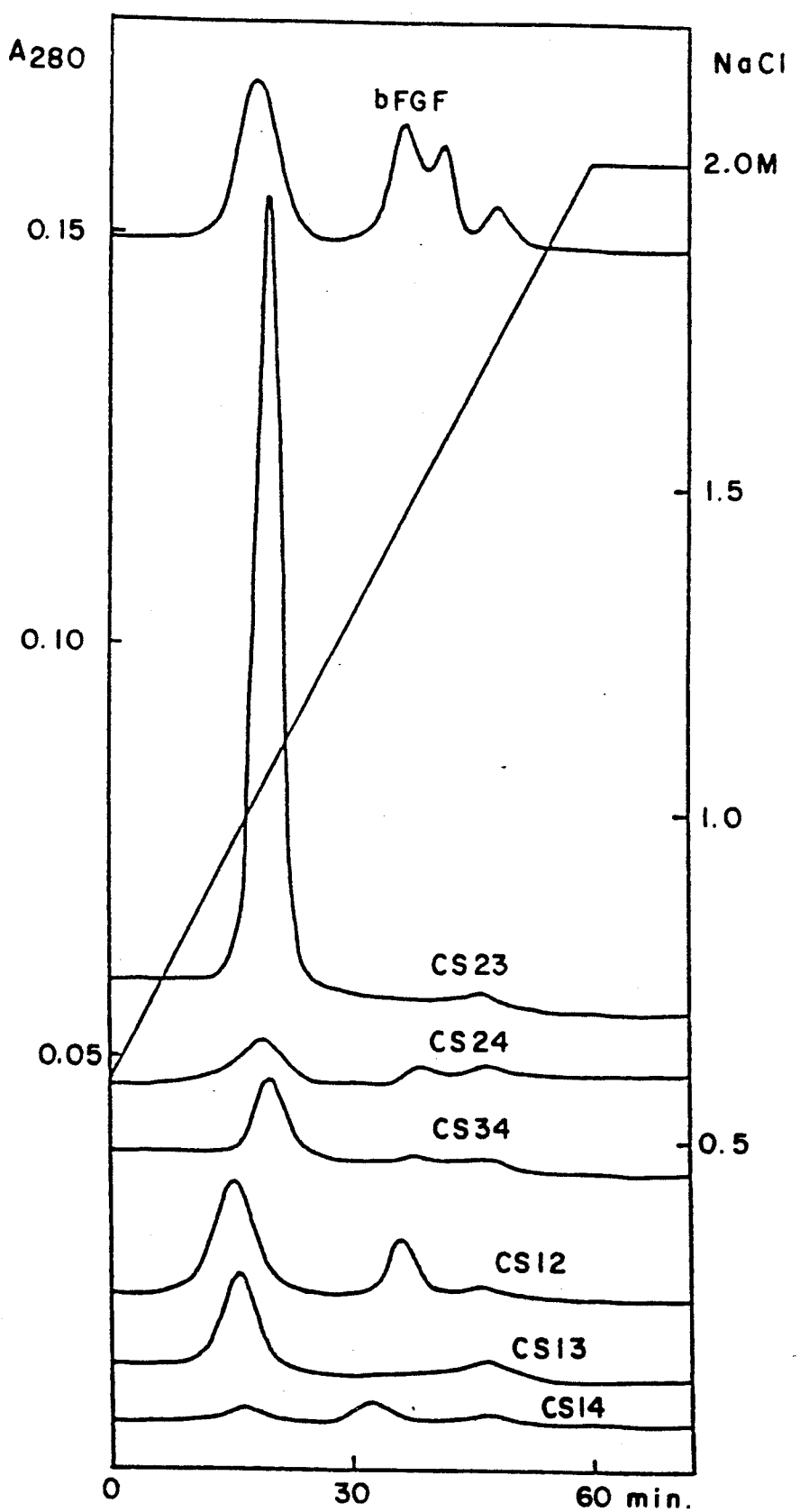
Figure 13:
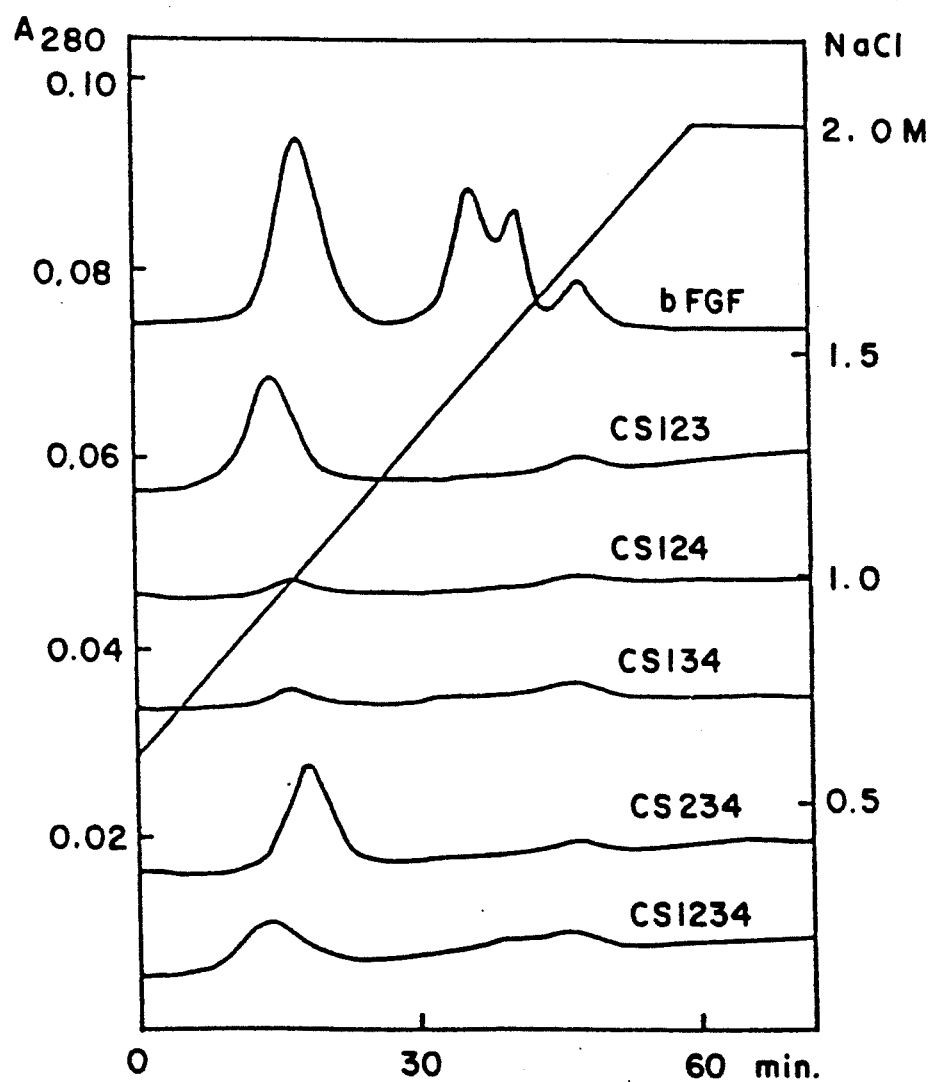

The elution patterns respective muteins are shown in FIGS. 11, 12, and 13. In these figures, the ordinates represent absorptions for $OD_{280}$ and NaCl concentrations in the gradient. The abscissas represent times, gradient elution being initiated on the time-0 point. Peak fractions were collected, and their FGF activities were investigated. The post-purification specific activities thereof are shown in Table 9.

TABLE 9

| Mutein | Specific Activity (mg-ptFGF/mg protein) |
|---|---|
| CS1 | 0.4 |
| CS2 | 0.9 |
| CS3 | 1.0 |
| CS4 | 1.0 |
| CS12 | 0.5 |
| CS13 | 0.5 |
| CS14 | 0.3 |
| CS23 | 1.1 |
| CS24 | 0.8 |
| CS34 | 0.5 |
| CS123 | 0.4 |
| CS124 | 0.1 |
| CS134 | 0.5 |
| CS234 | 0.9 |
| CS1234 | 0.1 |
| rhbFGF | 1.0 |

In Table 9, the specific activities are shown on the basis of the FGF activity of bovine brain-derived FGF (purity, not less than 95%) produced by Takara Shuzo Co., Ltd.

In all muteins, the peak corresponding to Peak I of bFGF was eluted at an elution time between 15 and 25 minutes. This can also be detected as a single band at the position of about 17,000 molecular weight in 17.25% SDS polyacrylamide gel electrophoresis.

What is claimed is:

1. A method of treating a mammal having an ulcerating disease of the gastrointestinal tract or a disease which is FGF-responsive in an acidic environment, which comprises administering an effective amount of an acid-resistant FGF composition to said mammal.

2. A method according to claim 1, wherein the method is to treat a mammal having an ulcerating disease of the gastrointestinal tract, which comprises administering an effective amount of an acid-resistant FGF composition to said mammal.

3. The method according to claim 1 or 2, wherein the acid-resistant FGF composition is selected from the group of native FGF in combination with a stabilizing agent, acid-resistant FGF or acid-resistant FGF in combination with a stabilizing agent.

4. The method according to claim 3, wherein the acid-resistant FGF comprises the rhbFGF mutein CS23.

5. The method according to claim 2, wherein the ulcerating disease of the gastrointestinal tract comprises regional ileitis.

6. The method according to claim 2, wherein the ulcerating disease of the gastrointestinal tract comprises ulcerated colitis.

7. The method according to claim 2, wherein the ulcerating disease of the gastrointestinal tract comprises a peptic ulcer.

8. The method according to claim 7, wherein the peptic ulcer is duodenal.

9. The method according to claim 7, wherein the peptic ulcer is gastric.

10. The method according to claim 3, wherein the mammal is a human, the composition is administered orally and the amount of the acid-resistant FGF protein component of the composition is between about 0.1 $\mu$g and 30 mg per day.

11. The method according to claim 10, wherein the amount of the acid-resistant FGF protein component is between about 1 $\mu$g and 3 mg per day.

12. The method according to claim 11, wherein the amount of the acid-resistant FGF protein component is between about 10 $\mu$g and 300 $\mu$g per day.

13. The method according to claim 3, wherein the stabilizing agent is selected from the group of glycosaminoglycan or glucan sulfate.

14. The method according to claim 13, wherein the glucan sulfate is selected from the group of dextran sulfate, cyclodextrin sulfate or B-1,3-glucan sulfate.

15. The method according to claim 3, wherein the acid-resistant FGF composition includes or is administered in combination with an antacid.

16. The method according to claim 3, wherein the acid-resistant FGF composition includes or is administered in combination with an antisecretory agent.

17. The method according to claim 16, wherein the antisecretory agent is selected from the group of cimetidine or ranitidine.

18. The method according to claim 3, wherein the acid-resistant FGF composition includes or is administered in combination with a cytoprotective agent.

* * * * *

UNITED STATES PATENT AND TRADEMARK OFFICE
CERTIFICATE OF CORRECTION

PATENT NO. : 5,175,147

DATED : December 29, 1992

INVENTOR(S) : Moses J. Folkman and Koichi Kato

It is certified that error appears in the above-identified patent and that said Letters Patent is hereby corrected as shown below:

Column 1, line 49, replace "oimetidine" with --cimitidine--.
Column 6, line 29, replace "22/1975" with --36422/1975--.
Column 6, line 40, replace "r,f" with --of--.
Column 6, line 59, replace "Alcalioenes" with --Alcaligenes--.
Column 10, line 39, replace "con.aining" with --containing--.
Column 11, line 62, replace "Tris-HCI" with --Tris-HCl--.
Column 12, line 16, replace "(NHhd)$_2$SO$_4$ with --(NH$_4$)$_2$SO$_4$--.

Column 12, line 66, replace "muoosasl" with --mucosal--.
Column 16, line 51, replace "enclodes" with --encodes--.
Column 17, line 6, replace "Kuokawa" with --Kurokawa--.
Column 17, line 31, replace "μm/ml" with --μg/ml--.
Column 17, line 33, replace "g/ml" with --μg/ml--
Column 17, line 39, replace "Nacl" with --NaCl--.
Column 19, line 11, replace "SSDNA" with --ssDNA--.
Column 21, line 31, replace "wall" with --well--.

UNITED STATES PATENT AND TRADEMARK OFFICE
CERTIFICATE OF CORRECTION

PATENT NO. : 5,175,147

DATED : December 29, 1992

INVENTOR(S) : Moses J. Folkman and Koichi Kato

It is certified that error appears in the above-identified patent and that said Letters Patent is hereby corrected as shown below:

Column 2, line 29, replace "TB975" with --pTB975--.
Column 3, line 48, replace "constitueny" with --constituent--.
Column 3, line 49, replace "Pro is comprising" with --Pro comprising--.
Column 3, line 52, replace "Senoo" with --Seno--.
Column 4, line 25, replace "pharmaceutiaclly" with --pharmaceutically--.
Column 6, line 47, replace "Alcaligenus" with --Alcaligenes--.
Column 7, line 19, replace "W/W" with --w/w--.
Column 7, line 20, replace "W/W" with --w/w--.
Column 10, line 49, replace "remaining control" with --control group--.
Column 11, line 8, replace "weight 7500" with --weight of 7500--.
Column 11, line 32, replace "PET3c" with --pET3c--.
Column 12, line 23, replace "m./min." with --ml/min.--.
Column 12, line 25, replace "pruified" with --purified--.
Column 12, line 39, replace "[3H]" with --[$^3$H]--.
Column 12, line 49, replace "JcI" with --Jcl--.
Column 13, line 20, replace "significant less" with --significant--.
Column 13, line 61, replace "induded" with --induced--.
Column 13, line 64, replace "administered 50" with --administered with 50--.
Column 15, line 11, replace "fidings" with --findings--.

UNITED STATES PATENT AND TRADEMARK OFFICE
CERTIFICATE OF CORRECTION

PATENT NO. : 5,175,147  
DATED : December 29, 1992  
INVENTOR(S) : Moses J. Folkman and Koichi Kato Page 3 Of 3

It is certified that error appears in the above-indentified patent and that said Letters Patent is hereby corrected as shown below:

Column 17, line 44, replace "Sorval" with --Sorvall --.

Column 18, line 5, replace "curved" with --curves --.

Column 18, line 64, replace "of" with --for --.

Signed and Sealed this

Twenty-eighth Day of December, 1993

Attest:

BRUCE LEHMAN

*Attesting Officer*  *Commissioner of Patents and Trademarks*